United States Patent [19]
Tam

[11] Patent Number: 6,117,839
[45] Date of Patent: *Sep. 12, 2000

[54] BONE STIMULATING FACTOR

[75] Inventor: Cherk Shing Tam, Oakville, Canada

[73] Assignee: Gensci Regeneration Sciences, Inc., Ontario, Canada

[*] Notice: This patent is subject to a terminal disclaimer.

[21] Appl. No.: 08/763,458

[22] Filed: Dec. 11, 1996

Related U.S. Application Data

[63] Continuation-in-part of application No. 08/487,074, Jun. 7, 1995, Pat. No. 5,880,094.

[51] Int. Cl.[7] .............................. A61K 38/13; C07K 14/00
[52] U.S. Cl. ................................ 514/12; 514/13; 514/14; 514/15; 530/300; 530/350
[58] Field of Search ................................. 530/300, 350; 514/12, 15, 13, 14

[56] References Cited

U.S. PATENT DOCUMENTS

| | | | |
|---|---|---|---|
| 5,461,034 | 10/1995 | Rodan et al. | 514/14 |
| 5,578,569 | 11/1996 | Tam | 514/12 |
| 5,661,127 | 8/1997 | Bhatnagar et al. | 514/6 |

FOREIGN PATENT DOCUMENTS

| | | |
|---|---|---|
| 2231872 | 11/1990 | United Kingdom . |
| 90/06321 | 6/1990 | WIPO . |
| 95/28172 | 10/1995 | WIPO . |

OTHER PUBLICATIONS

Sambrook et al. Moleular cloning: a laboratory manual. 2nd ed. Cold Spring Harbor, N.Y. Cold Spring Harbor Laboratory Press, 1989.

Dart et al. Transforming growth factors from a human tumor cell: characterization of transforming growth factor beta and identification of high molecular weight transforming growth factor alpha. Biochemistry, (Oct. 8, 1985) 24 (21) 5925–31.

Noda et al. In vivo stimulation of bone formation by transforming growth factor–beta. Endocrinology, (Jun. 1989) 124(6) 2991–4.

A. Walz et al., "Generation of the Neutrophil–Activating Peptide NAP–2 from Platelet Basic Protein or Connective Issue–3 Activating Peptide III Through Monocyte Proteases", Journal of Med., vol. 171, Feb. 1990, pp. 449–454.

C.W. Castor et al., "Connective Tissue Activation—Biologically Active Cleavage Products of CTAP–III From Human Platelets", Biochemical and Biophysical Research Communications, vol. 163, No. 2, 1989, pp. 1071–1078.

G. Begg et al., "Complete Covalent Structure of Human β–Thromboglobulin", Structure of β–Thromboglobulin, vol. 17, No. 9, 1978, pp. 1739–1744.

C.W. Castor et al., "Structural and Biological Chacteristics of Connective Tissue Activating Peptide (CTAP–III), a Major Human Platelet-3 derived Growth Factor", Proc. Natl. Acad. Sci. USA, vol. 80, Fed. 1983, pp. 765–769.

C.W. Castor et al., "Connective Tissue Activation", Arthritis & Rheumatism, vol. 35, No. 7, Jul. 1992, pp. 783–793.

*Primary Examiner*—Elizabeth Kemmerer
*Assistant Examiner*—David S. Romeo
*Attorney, Agent, or Firm*—Foley & Lardner

[57] ABSTRACT

Polypeptides which stimulate bone growth: Gly Ile Gly Lys Arg Thr Asn Glu His Thr Ala Asp Cys Lys Ile Lys Pro Asn Thr Leu His Lys Lys Ala Ala Glu Thr Leu Met Val Leu Asp Gln Asn Gln Pro (SEQ ID NO:1) and subsequences, particularly Arg Thr Asn Glu His Thr Ala Asp Cys Lys (SEQ ID NO:9) and associated nucleotide sequences, methods of preparation and use, antibodies and kits.

7 Claims, 10 Drawing Sheets

FIGURE 15

Active Sequences:

```
                   1         5         10        15        20        25        30        35
SEQ ID NO:1        G I G K R T N E H T A D C K I K P N T L H K K A A E T L M V L D Q N Q P
SEQ ID NO:3        G I G K R T N E H T A D A K I K P N T L H K K A A E T L M V L D Q N Q P
SEQ ID NO:4        G I G K R T N E H T A D C K I K P N T L H K K A A E T L M V
SEQ ID NO:5        G I G K R T N E H T A D C K I K P N T L H K K A A
SEQ ID NO:6        G I G K R T N E H T A D C K I
SEQ ID NO:7        G I G K R T N E H T A D C K
SEQ ID NO:8        G I G K R T N E H T A D C K
SEQ ID NO:9              R T N E H T A D C K
SEQ ID NO:24       Ac - R T N E H T A D C K - NH2
SEQ ID NO:25       Ac - R T N E H T A E C K - NH2
SEQ ID NO:26       Ac - R T N Q E H T A E C K - NH2
SEQ ID NO:27       Ac - R T N Q E H T A D C K - NH2

SEQ ID NO:10                                       L H K K A A E T L M V L D Q N
SEQ ID NO:11                                       L H K K A A E T L M V L D Q N
SEQ ID NO:12                                       L H K K A A E T L M V L D Q
SEQ ID NO:13                                       L H K K A A E T L M V L D Q
SEQ ID NO:14                                       L H K K A A E T L M V L D
SEQ ID NO:15                   T A D C K I K P N T L H K K A A E T L M V L D Q N
SEQ ID NO:16             R T N E H T A D C K I
```

BONE STIMULATING FACTOR

This application is a continuation-in-part of prior application Ser. No. 08/487,074, U.S. Pat. No. 5,880,094, filed Jun. 7, 1995 which is incorporated herein by reference.

The present invention relates to polypeptides which stimulate bone growth.

Understanding of issues related to bone growth and strength has progressed over the years, a summary being provided in international patent application No. PCT/CA 94/00144, published under international publication No. WO 94/20615 on Sep. 15, 1994.

Various approaches to treatment of diseases involving reduction of bone mass and accompanying disorders are exemplified in the patent literature. For example, U.S. Pat. No. 4,877,864, issued Oct. 31, 1989 describes human and bovine "bone inductive factors." International patent application published Sep. 17, 1992 under Ser. No. 92/15615 describes a protein derived from a porcine pancreas which acts to depress serum calcium levels for treatment of bone disorders that cause elevation of serum calcium levels. European Patent Application No. 504 938 published Sep. 23, 1992 describes the use of di- or tripeptides which inhibit cysteine protease in the treatment of bone diseases. International patent application published Sep. 3, 1992 under Ser. No. 92/14481 discloses a composition for inducing bone growth, the composition containing activin and bone morphogenic protein. European Patent Application No. 499 242 published Aug. 19, 1992 describes the use of cell growth factor compositions thought to be useful in bone diseases involving bone mass reduction because they cause osteoblast proliferation. International patent application published Jun. 25, 1992 under Ser. No. 92/10515 1992 describes a drug containing the human N-terminal parathyroid hormone (PTH) fragment 1–37. European Patent Application No. 451 867 published Sep. 16, 1991 describes parathyroid hormone peptide antagonists for treating dysbolism associated with calcium or phosphoric acid, such as osteoporosis. U.S. Pat. No. 5,461,034 issued Oct. 24, 1995 to Yissum Research Development Company of the Hebrew University of Jerusalem describes osteogenic growth polypeptides identified from regenerating bone marrow.

A relatively short half life of PTH in the blood serum and the positive effect of intermittent PTH injection on bone volume led the present investigator to the hypothesis that PTH may in some way lead to induction of a second factor into the circulatory system. The presence of such a second factor in blood serum of rats and of humans has thus been investigated.

It has been found possible to isolate from rat blood serum a polypeptide substance which, upon administration to rats incapable of producing PTH (parathyroidectomized rats), produces an increase in the observed bone mineral apposition rate. A nucleic acid probe, based on the amino acid sequence of the rat peptide was synthesized and used to screen a human liver cDNA fetal library in order to isolate a human nucleic acid sequence coding for a human bone apposition polypeptide. A polypeptide derived from the nucleic acid sequence was thus chemically synthesized according to the derived sequence Gly Ile Gly Lys Arg Thr Asn Glu His Thr Ala Asp Cys Lys Ile Lys Pro Asn Thr Leu His Lys Lys Ala Ala Glu Thr Leu Met Val Leu Asp Gln Asn Gln Pro (SEQ ID NO:1). It has been observed that the bone apposition rate in intact rats increases in a dose dependent fashion upon administration of this chemically synthesized compound. Reduced bone growth, normally observed for ovariectomized rats, was observed not to occur in rats after being administered with the polypeptide over a four week period beginning two weeks after ovariectomization. Bone calcium density was found to be maintained in ovariectomized rats administered with the polypeptide over an eight week period beginning eight weeks after ovariectomization.

It is thought possible that the active polypeptide is a dimer of the foregoing sequence, there being evidence of significant dimer formation, presumably due to a disulfide bridge between two polypeptides having the sequence shown.

A modified form of the polypeptide containing a cys-ala substitution was thus synthesized: Gly Ile Gly Lys Arg Thr Asn Glu His Thr Ala Asp Ala Lys Ile Lys Pro Asn Thr Leu His Lys Lys Ala Ala Glu Thr Leu Met Val Leu Asp Gln Asn Gln Pro (SEQ ID NO:3). Some of the bone stimulatory effects of the "normal" polypeptide (SEQ ID NO:1) were found for the modified polypeptide.

In other experiments, the bone mineral apposition rate in rats administered with rabbit antibodies to the normal polypeptide (SEQ ID NO:1) was found to be suppressed. The suppression was found to be attenuated in rats administered with both the normal polypeptide and antibodies to same.

Further, certain polypeptide fragments of the normal polypeptide (SEQ ID NO:1) have been synthesized and each has been found to have bone stimulatory effects:

SEQ ID NO:4:
Gly Ile Gly Lys Arg Thr Asn Glu His Thr Ala Asp Cys Lys Ile Lys Pro Asn Thr Leu His Lys Lys Ala Ala Glu Thr Leu Met Val

SEQ ID NO:5:
Gly Ile Gly Lys Arg Thr Asn Glu His Thr Ala Asp Cys Lys Ile Lys Pro Asn Thr Leu His Lys Lys Ala Ala

SEQ ID NO:6:
Gly Ile Gly Lys Arg Thr Asn Glu His Thr Ala Asp Cys Lys Ile Lys Pro Asn Thr Leu

SEQ ID NO:7:
Gly Ile Gly Lys Arg Thr Asn Glu His Thr Ala Asp Cys Lys Ile

SEQ ID NO:8:
Gly Ile Gly Lys Arg Thr Asn Glu His Thr Ala Asp Cys Lys

SEQ ID NO:9:
Arg Thr Asn Glu His Thr Ala Asp Cys Lys

Further, the polypeptide identified as SEQ ID NO: 7 has been found to increase bone calcium content of ovariectomized rats when administered over a period of eight or twelve weeks.

Other polypeptide fragments of the normal polypeptide (SEQ ID NO: 1) have also been synthesized and have been found to lack the bone stimulatory effect found for the normal polypeptide:

SEQ ID NO:10:
Leu His Lys Lys Ala Ala Glu Thr Leu Met Val Leu Asp Gln Asn Gln

SEQ ID NO:11:
Leu His Lys Lys Ala Ala Glu Thr Leu Met Val Leu Asp Gln Asn

SEQ ID NO:12:
Leu His Lys Lys Ala Ala Glu Thr Leu Met Val Leu Asp Gln

SEQ ID NO:13:
Leu His Lys Lys Ala Ala Glu Thr Leu Met Val Leu Asp

SEQ ID NO:14:
Thr Ala Asp Cys Lys Ile Lys Pro Asn Thr Leu His Lys Lys Ala Ala Glu Thr Leu Met Val Leu Asp

SEQ ID NO:15:
Arg Thr Asn Glu His Thr Ala Asp Cys Lys Ile Lys Pro Asn Thr Leu His Lys Lys Ala Ala Glu Thr Leu Met Val Leu Asp Gln Asn

SEQ ID NO:16:
Arg Thr Asn Glu His Thr Ala Asp Cys Lys Ile

The polypeptide identified as SEQ ID NO:9 was modified to include a protecting group at each end. The N-terminus was thus acetylated and C-terminus was amidated. The activity of this protected polypeptide, identified as SEQ ID NO:24, was found to increase the bone mineral apposition rate in rats beyond that observed for each of the polypeptides identified as SEQ ID NOS: 1,7 and 9.

It has been reported that histidine and cysteine residues can effect degradation of asparaginyl- and aspartyl-containing polypeptides in the absence of catalytic enzymes [Int. J. Peptide Protein Res. 45, 1995, 547,553]. The following analogues of the polypeptide identified as SEQ ID NO:9 were tested, for stability and for effects on bone mineral apposition rate:

SEQ ID NO:25:
$CH_3CO$—Arg Thr Asn Glu His Thr Ala Glu Cys Lys—$NH_2$
SEQ ID NO:26:
$CH_3CO$—Arg Thr Gln Glu His Thr Ala Glu Cys Lys—$NH_2$
SEQ ID NO:27:
$CH_3CO$—Arg Thr Gln Glu His Thr Ala Asp Cys Lys—$NH_2$

In terms of stability under the various conditions tested, the polypeptides identified as SEQ ID NOS:25 and 26 were found to be more stable than those identified as SEQ ID NOS:9, 7 and 24. The polypeptide identified as SEQ ID NO:27 was found to be less stable than any of SEQ ID NOS: 7, 9, 24, 25 and 26.

Each of the polypeptides identified as SEQ ID NOS:24, 25, 26 and 27 were found to increase the bone apposition rate over that observed for control rats.

Polypeptide sequences corresponding to SEQ ID NOS:25, 26 and 27 in which the terminal amino acid residues are not protected are referred to herein as SEQ ID NOS:28, 29 and 30, respectively.

The present invention thus includes a polypeptide having an amino acid sequence corresponding to SEQ ID NO:1 with (a) from one to about four 4 amino acids deleted from the N-terminus of SEQ ID NO:1 (b) one to about 22 amino acids deleted from the C-terminus of SEQ ID NO:1, or both (a) and (b); or a functionally equivalent homologue. Correspondingly, the invention includes a polypeptide having an amino acid sequence corresponding to SEQ ID NO:3 with (a) from one to about four 4 amino acids deleted from the N-terminus of SEQ ID NO:3 (b) one to about 22 amino acids deleted from the C-terminus of SEQ ID NO:3, or both (a) and (b); or a functionally equivalent homologue. Sequence homology in polypeptides and proteins is understood to those skilled in the art, as discussed, for example in Molecular Cell Biology (H. Lodish, D. Baltimore, A. Berk, S. L. Zipursky, P. Matsudaira and J. Darnell, Scientific American Books, New York City, Third Edition, 1995). Likewise, the invention includes a polypeptide having an amino acid sequence corresponding to SEQ ID NO:4 with (a) up to about four 4 amino acids deleted from the N-terminus of SEQ ID NO:4, (b) up to about 16 amino acids deleted from the C-terminus of SEQ ID NO:4, or both (a) and (b); or a functionally equivalent homologue. The invention includes a polypeptide having an amino acid sequence corresponding to SEQ ID NO:5 with (a) up to about four 4 amino acids deleted from the N-terminus of SEQ ID NO:5, (b) up to about 11 amino acids deleted from the C-terminus of SEQ ID NO:5, or both (a) and (b); or a functionally equivalent homologue. The invention includes a polypeptide having an amino acid sequence corresponding to SEQ ID NO:6 with (a) up to about four 4 amino acids deleted from the N-terminus of SEQ ID NO:6, (b) up to about 5 amino acids deleted from the C-terminus of SEQ ID NO:6, or both (a) and (b); or a functionally equivalent homologue. The invention includes a polypeptide having an amino acid sequence corresponding to SEQ ID NO:7 with (a) up to about four 4 amino acids deleted from the N-terminus of SEQ ID NO:7, (b) up to about 1 amino acids deleted from the C-terminus of SEQ ID NO:4, or both (a) and (b); or a functionally equivalent homologue. The invention also includes a polypeptide having an amino acid sequence corresponding to SEQ ID NO:8 with up to about four 4 amino acids deleted from the N-terminus or a functionally equivalent homologue. The invention includes a polypeptide having an amino acid sequence corresponding to SEQ ID NO:9 or a functionally equivalent homologue thereof.

The invention includes a polypeptide up to about 30 amino acids in length comprising an amino acid sequence corresponding to SEQ ID NO:9 or a functionally equivalent homologue thereof which promotes bone growth in mammals The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide of up to about 25 amino acids in length comprising an amino acid sequence corresponding to SEQ ID NO:9 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

Alternatively, the invention includes a polypeptide of up to about 20 amino acids in length comprising an amino acid sequence corresponding to SEQ ID NO:9 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide of up to about 15 amino acids in length comprising an amino acid sequence corresponding to SEQ ID NO:9 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide about 10 amino acids in length comprising an amino acid sequence corresponding to SEQ ID NO:9 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms. The invention includes a polypeptide having an amino acid sequence corresponding to SEQ ID NO:24.

The invention includes a polypeptide up to about 30 amino acids in length comprising an amino acid sequence corresponding to SEQ ID NO:28 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide of up to about 25 amino acids in length comprising an amino acid sequence corresponding to SEQ ID NO:28 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

Alternatively, the invention includes a polypeptide of up to about 20 amino acids in length comprising an amino acid sequence corresponding to SEQ ID NO:28 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide of up to about 15 amino acids in length comprising an amino acid sequence corresponding to SEQ ID NO:28 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide about 10 amino acids in length comprising an amino acid sequence corresponding to SEQ ID NO:28 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms. The invention includes a polypeptide having an amino acid sequence corresponding to SEQ ID NO:25.

The invention includes a polypeptide up to about 30 amino acids in length comprising an amino acid sequence corresponding to SEQ ID NO:29 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide of up to about 25 amino acids in length comprising an amino acid sequence corresponding to SEQ ID NO:29 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

Alternatively, the invention includes a polypeptide of up to about 20 amino acids in length comprising an amino acid sequence corresponding to SEQ ID NO:29 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide of up to about 15 amino acids in length comprising an amino acid sequence corresponding to SEQ ID NO:29 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide about 10 amino acids in length comprising an amino acid sequence corresponding to SEQ ID NO:29 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms. The invention includes a polypeptide having an amino acid sequence corresponding to SEQ ID NO:26.

The invention includes a polypeptide up to about 30 amino acids in length comprising an amino acid sequence corresponding to SEQ ID NO:30 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide of up to about 25 amino acids in length comprising an amino acid sequence corresponding to SEQ ID NO:30 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

Alternatively, the invention includes a polypeptide of up to about 20 amino acids in length comprising an amino acid sequence corresponding to SEQ ID NO:30 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide of up to about 15 amino acids in length comprising an amino acid sequence corresponding to SEQ ID NO:30 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms.

The invention includes a polypeptide about 10 amino acids in length comprising an amino acid sequence corresponding to SEQ ID NO:30 or a functionally equivalent homologue thereof which promotes bone growth in mammals. The polypeptide can have a protected terminal amino group, or a protected terminal carboxyl group, or both. The N-terminal protecting group can be an acetyl group. The C-terminal can be protected by conversion of the carboxyl group to an amide group, in which for example, the amino nitrogen thereof is bound to two hydrogen atoms. The invention includes a polypeptide having an amino acid sequence corresponding to SEQ ID NO:27.

Polypeptides of the present invention can be incorporated into larger polypeptide sequences in which there is repetition of active sequences in a single molecule.

The inventive polypeptide can be synthetic and the amino acid sequence can have a molecular weight in the range of from about 1000 to 4000.

The invention includes a polypeptide having a sequence of amino acids sufficiently duplicative of another, i.e., second polypeptide having an amino acid sequence corresponding to SEQ ID NO:1 (or SEQ ID NO:3) with (a) from one to about four 4 amino acids deleted from the N-terminus of SEQ ID NO:1 (or SEQ ID NO:3), (b) one to about 22 amino acids deleted from the C-terminus of SEQ ID NO:1 or (SEQ ID NO:3), or both (a) and (b), or a functionally equivalent homologue thereof, such that the polypeptide is encoded by a DNA that hybridizes under stringent conditions with DNA encoding the second polypeptide. The polypeptide can be up to about 30 amino acids in length, for example, and the sequence of that polypeptide can be repeated within a larger polypeptide, or contain other polypeptide sequences which are not by themselves stimulate bone growth. Such polypeptide could also be up to 25, 20, 15 or about 10 amino acids in length.

"Stringent hybridization conditions" takes on its common meaning to a person skilled in the art here. Appropriate stringency conditions which promote nucleic acid hybridization, for example, 6x sodium chloride/sodium citrate (SSC) at about 45° C. are known to those skilled in the art. The following examples are found in Current Protocols in Molecular Biology, John Wiley & Sons, NY (1989), 6.3.1–6.3.6: For 50 ml of a first suitable hybridization solution, mix together 24 ml formamide, 12 ml 20x SSC, 0.5 ml 2 M Tris-HCl pH 7.6, 0.5 ml 100x Denhardt's solution, 2.5 ml deionized $H_2O$, 10 ml 50% dextran sulfate, and 0.5 ml 10% SDS. A second suitable hybridization solution can be 1% crystalline BSA (fraction V), 1 mM EDTA, 0.5 M $Na_2HPO_4$ pH 7.2, 7% SDS. The salt concentration in the wash step can be selected from a low stringency of about 2x SSC at 50° C. to a high stringency of about 0.2x SSC at 50° C. Both of these wash solutions may contain 0.1% SDS. In addition, the temperature in the wash step can be increased from low stringency conditions at room temperature, about 22° C. to high stringency conditions, at about 65° C. The cited reference gives more detail, but appropriate wash stringency depends on degree of homology and length of probe. If homology is 100%, a high temperature (65° C. to 75° C.) may be used. If homology is low, lower wash temperatures must be used. However, if the probe is very short (<100bp), lower temperatures must be used even with 100% homology. In general, one starts washing at low temperatures (37° C. to 40° C.), and raises the temperature by 3–5° C. intervals until background is low enough not to be a major factor in autoradiography.

In another aspect the invention is a synthetic polypeptide having in vivo bone stimulatory activity in mammals and which increases mineral content (i.e., calcium) in bones of mammals, having an amino acid sequence which is at least about 19% conserved in relation to the amino acid sequence identified as SEQ ID NO:1 and having at least one amino acid deleted therefrom, or a functionally equivalent homologue.

The invention includes a synthetic polypeptide having in vivo bone stimulatory activity in mammals and which increases mineral content in bones of mammals, having an amino acid sequence which is at least about 22% conserved in relation to the amino acid sequence identified as SEQ ID NO:1 and having at least one amino acid deleted therefrom.

The invention includes a synthetic polypeptide having in vivo bone stimulatory activity in mammals and which increases mineral content in bones of mammals, having an amino acid sequence which is at least about 25% conserved in relation to the amino acid sequence identified as SEQ ID NO:1 and having at least one amino acid deleted therefrom.

The invention includes a synthetic polypeptide having in vivo bone stimulatory activity in mammals and which increases mineral content in bones of mammals, having an amino acid sequence which is at least about 28% conserved in relation to the amino acid sequence identified as SEQ ID NO:1 and having at least one amino acid deleted therefrom.

The invention includes any of the foregoing synthetic polypeptides in which at least six amino acids deleted from the polypeptide sequence; or in which at least eleven amino acids deleted from the sequence; or in which at least sixteen amino acids deleted from the sequence; or in which at least twenty-one amino acids deleted from the sequence; or in which at least twenty-six amino acids deleted from the sequence.

The invention includes a polypeptide having a sequence of amino acids sufficiently duplicative of one of the foregoing synthetic polypeptides such that the polypeptide is encoded by a DNA that hybridizes under stringent conditions with DNA encoding the synthetic polypeptide.

In another aspect the invention is a polypeptide exhibiting bone stimulatory activity in mammals, the polypeptide having the sequence identified as SEQ ID NO:1, SEQ ID NO:3, SEQ ID NO:4, SEQ ID NO:5, SEQ ID NO:4, SEQ ID NO:6, SEQ ID NO:7, SEQ ID NO:8, SEQ ID NO:9; SEQ ID NO:24; SEQ ID NO:25; SEQ ID NO:26; SEQ ID NO:27; SEQ ID NO:28; SEQ ID NO:29; or SEQ ID NO:30; analogues thereof wherein the amino acids in the sequence may be substituted, deleted or added, so long as the bone stimulatory activity in mammals derived the three dimensional structure of the sequence is preserved; and conjugates of each of the polypeptides or analogues thereof, wherein if the polypeptide sequence has that identified as SEQ ID NO:1, then there is at least one amino acid deleted therefrom. The invention includes a polypeptide that has a sequence of amino acids sufficiently duplicative of such a bone stimulatory polypeptide (or a functionally equivalent homologue thereof) that the polypeptide is encoded by a DNA that hybridizes under stringent conditions with DNA encoding the bone stimulatory polypeptide.

In another aspect, the invention is a polypeptide that includes an amino acid sequence that is between 19% and 90% conserved in relation to the amino acid sequence identified as SEQ ID NO:1; or an amino acid sequence that is between 19% and 86% conserved in relation to the amino acid sequence identified as SEQ ID NO:1; or an amino acid sequence that is between 19% and 69% conserved in relation to the amino acid sequence identified as SEQ ID NO:1; or an amino acid sequence that is between 19% and 56% conserved in relation to the amino acid sequence identified as SEQ ID NO:1; or an amino acid sequence that is between 19% and 42% conserved in relation to the amino acid sequence identified as SEQ ID NO:1; or an amino acid sequence that is between 19% and 39% conserved in relation to the amino acid sequence identified as SEQ ID NO:1; or an amino acid sequence that is between 19% and 28% conserved in relation to the amino acid sequence identified as SEQ ID NO:1; or an amino acid sequence that is between 28% and 90% conserved in relation to the amino acid sequence identified as SEQ ID NO:1; or an amino acid sequence that is between 28% and 86% conserved in relation to the amino acid sequence identified as SEQ ID NO:1; or an amino acid sequence that is between 28% and 69% conserved in relation to the amino acid sequence identified as SEQ ID NO:1; or an amino acid sequence that is between 28% and 56% conserved in relation to the amino acid sequence identified as SEQ ID NO:1; or an amino acid sequence that is between 28% and 42% conserved in relation to the amino acid sequence identified as SEQ ID NO:1; or an amino acid sequence that is between 28% and 39% conserved in relation to the amino acid sequence identified as SEQ ID NO:1; or a functionally equivalent homologue that has bone stimulatory activity in a mammal.

The polypeptide can be a chimeric bone stimulating factor that includes any of the amino acid sequences described above as part of the invention.

The invention includes an agent for use in prevention and treatment of a bone reduction related disease that includes any polypeptide described above as part of the invention, including of course a chimeric polypeptide, as an active ingredient.

The invention is thus also a pharmaceutical composition for promoting bone growth, having a therapeutically effective amount of any polypeptide described above as part of the invention.

The invention includes a method of increasing bone growth in a mammal by administering a therapeutically effective amount of a polypeptide (or a pharmaceutical composition including the polypeptide) described above as part of the invention.

The invention includes the treatment of osteoporosis, promotion of bone growth in a mammal or treatment of a human of a bone reduction related disease.

The invention includes the use of a polypeptide having a sequence according to any polypeptide of the invention in the preparation of a medicament for use in promoting bone growth or the treatment of osteoporosis, etc.

The invention includes a diagnostic kit for determining the presence of a polypeptide of the invention, in which the kit includes an antibody to a polypeptide (or polypeptides) linked to a reporter system wherein the reporter system produces a detectable response when a predetermined amount of the polypeptide (or polypeptides) and the antibody become bound together.

The invention includes an antibody which binds to a polypeptide of the invention. Particularly, the invention includes an antibody which binds to such a polypeptide when the antibody is synthesized using the polypeptide.

The invention includes molecules, such as isolated nucleotide sequences related to polypeptides of the invention. For example, the invention includes an isolated DNA fragment which encodes the expression of any of the polypeptides of the invention. It is of course understood that such fragments can vary from one another due to the degeneracy of the genetic code. Further, the invention includes a vector that has incorporated into it any such DNA sequence.

The invention includes an isolated DNA sequence encoding any amino acid sequence of the invention, or an analogue thereof, wherein the amino acids in the sequence may be substituted, deleted or added, so long as bone stimulatory activity in mammals derived from the three dimensional conformation of the sequence is preserved in a polypeptide having the amino acid sequence; sequences which hybridize to the DNA and encode an amino acid sequence of a polypeptide which displays bone stimulatory activity in mammals; and and DNA which differs from the sequence due to the degeneracy of the genetic code.

The invention thus includes processes of producing any polypeptide of the invention, including a process which includes: a) preparing a DNA fragment containing a nucleotide sequence that encodes such a polypeptide; b) incorporating the DNA fragment into an expression vector to obtain a recombinant DNA fragment which contains the DNA fragment and is capable of undergoing replication; c) transforming a host cell with the recombinant DNA fragment to isolate a transformant which can express the polypeptide; and d) culturing the transformant to allow the transformant to produce the polypeptide and recovering the polypeptide from resulting cultured mixture.

BRIEF DESCRIPTION OF THE DRAWINGS

In the following description, reference is made to accompanying drawings, wherein, FIG. 1 graphically depicts the bone mineral apposition rate ($\mu$m per day) in rats provided with the chemically synthesized human N-acetyl (N-terminus) polypeptide (SEQ ID NO:2) through implantation in parathyroidectomized rats. The error bars indicate ±1 standard deviation (S.D.). The value of p was less than 0.001.

Group B rats were treated with the same antibodies and the polypeptide itself. Group C is the control group. The error bars indicate ±1 standard deviation (S.D.).

Figure 6:
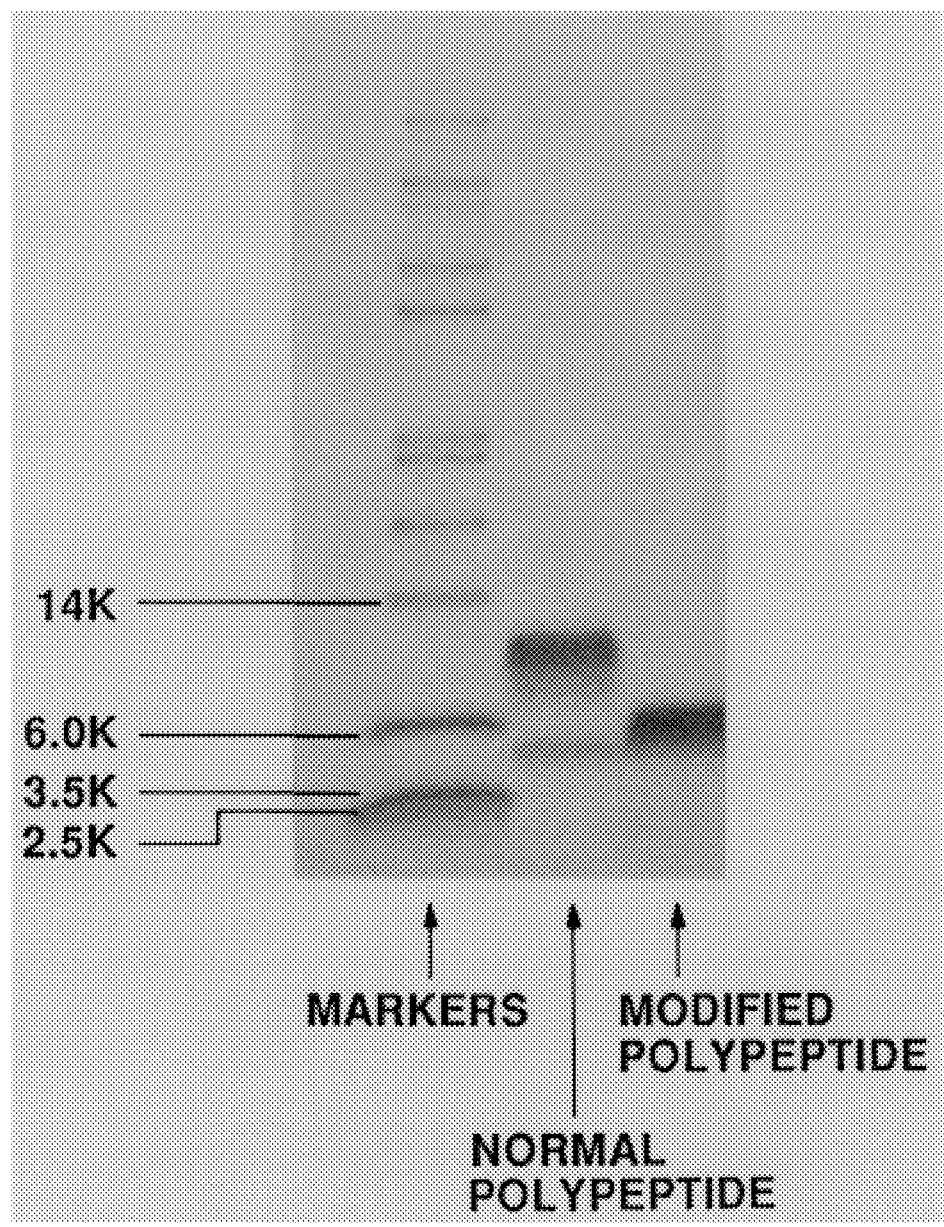

FIG. 6 shows a tricine SDS electrophoretic gel of the human chemically synthesized polypeptide (SEQ ID NO:1) and the same polypeptide containing a cys→ala substitution (SEQ ID NO:3).

Figure 7:
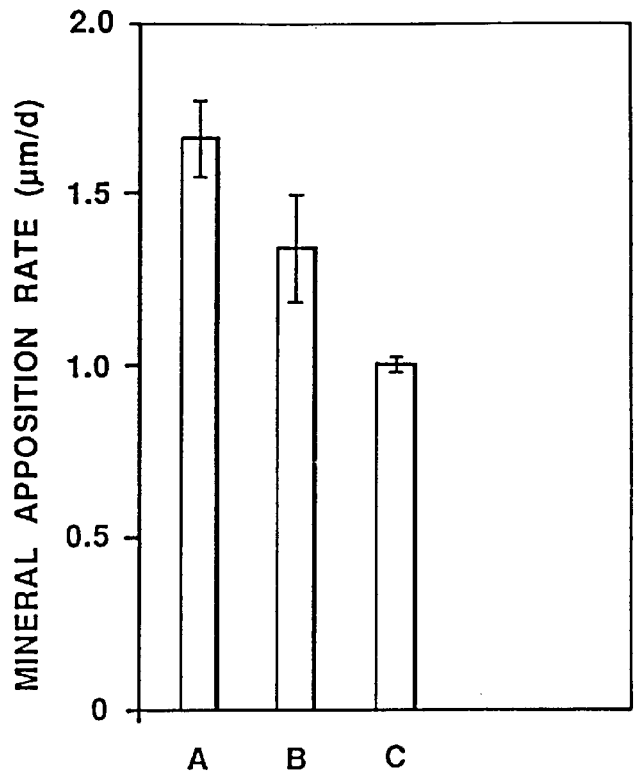

FIG. 7 graphically depicts the bone mineral apposition rate ($\mu$m per day) in rats injected with the chemically synthesized human polypeptide (SEQ ID NO:1), Group A; the modified chemically synthesized human polypeptide (SEQ ID NO:3), Group B; and control, Group C. (N=6 for all groups). The error bars indicate ±1 standard deviation (S.D.).

Figure 8:
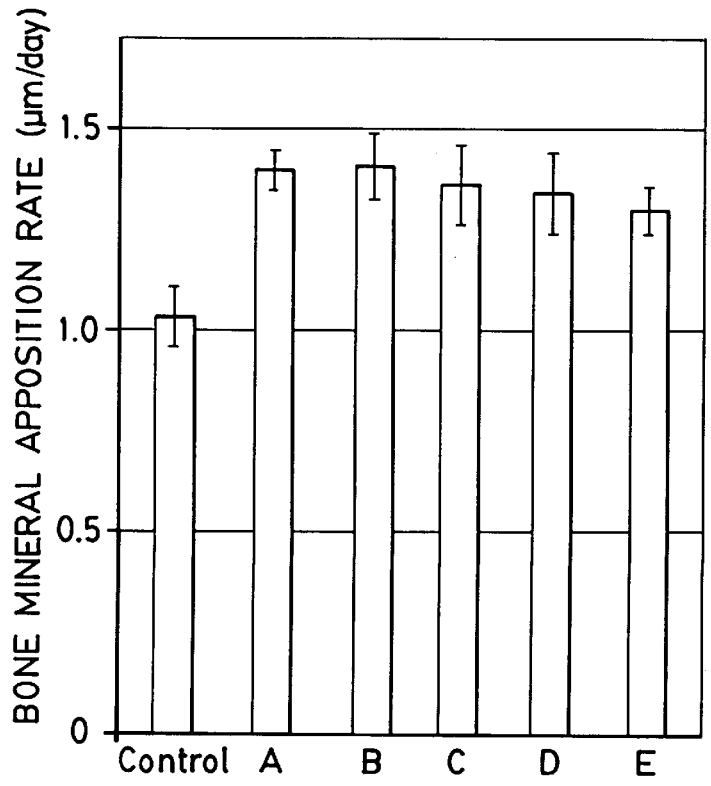

FIG. 8 graphically depicts the bone mineral apposition rate ($\mu$m per day) in rats injected with N-terminus chemically synthesized polypeptides: SEQ ID NO:1 (Group A); SEQ ID NO:7 (Group B); SEQ ID NO:6 (Group C); SEQ ID NO:5 (Group D); and SEQ ID NO:4 (Group E). (N=6 for all groups). The error bars indicate ±1 standard deviation (S.D.).

Figure 9:
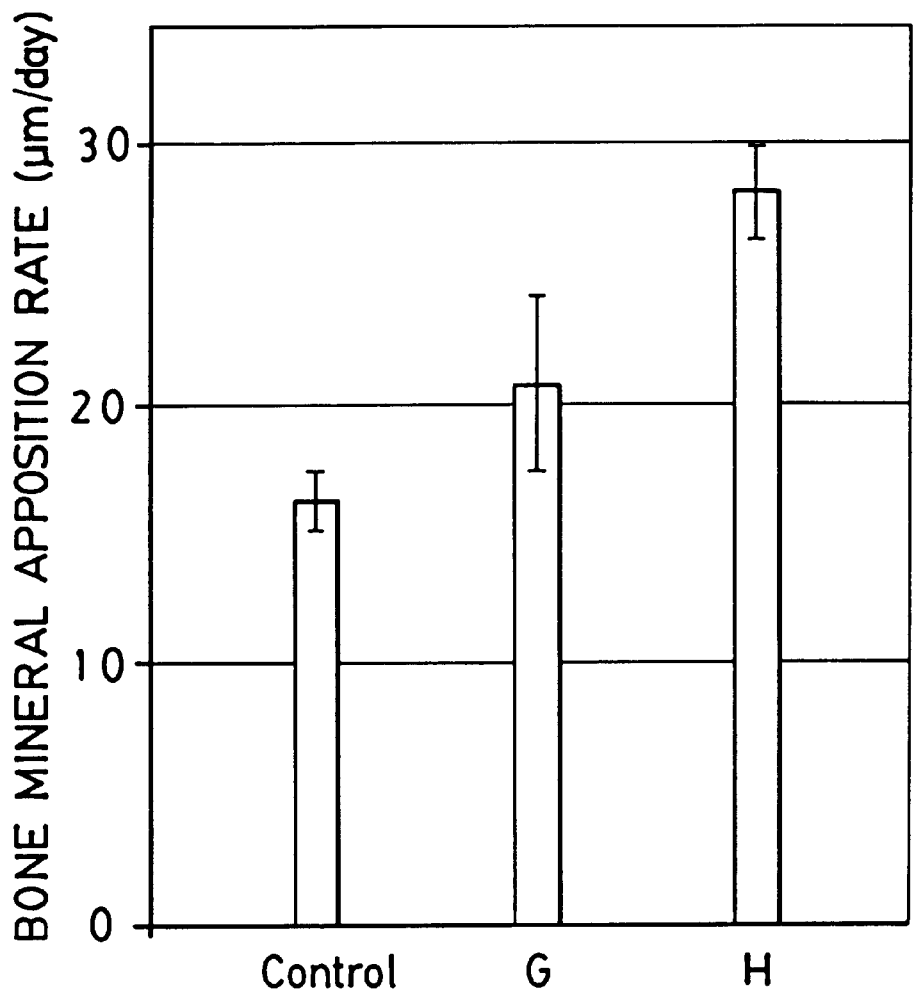

FIG. 9 graphically depicts the bone mineral apposition rate ($\mu$m per day) in rats injection with chemically synthesized polypeptides: SEQ ID NO:8 (Group G); SEQ ID NO:9 (Group H).

Figure 10:
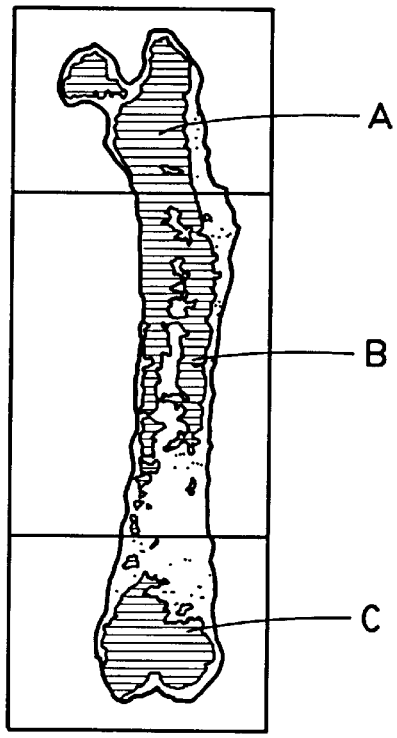

FIG. 10 is a DEXA image of a right femur of a rat showing scanned areas: A, proximal end; B, diaphysis; and C, distal end.

Figure 11:
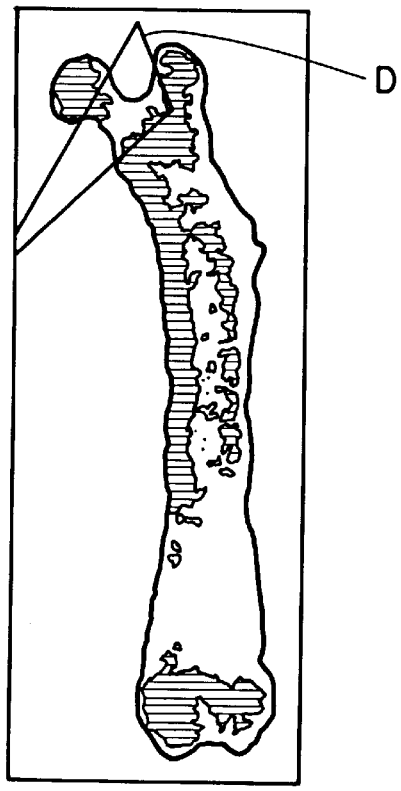

FIG. 11 is a DEXA image of a right femur of a rat showing scanned neck area.

Figure 12:
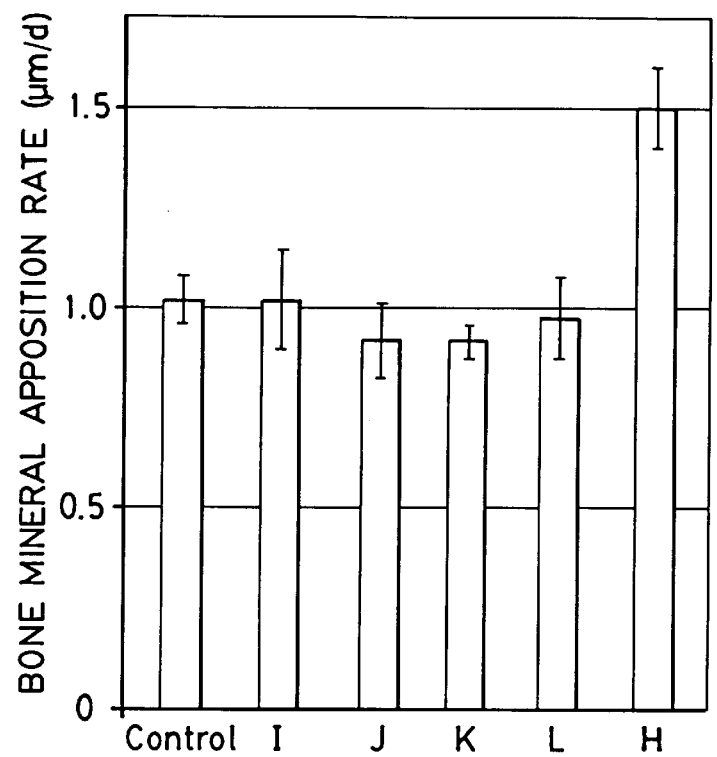

FIG. 12 graphically depicts the bone mineral apposition rate ($\mu$m per day) in rats injected with non-N-terminus chemically synthesized polypeptide fragments SEQ ID NO:1 (Group H); SEQ ID NO:16 (Group I); SEQ ID NO:15 (Group J); SEQ ID NO:14 (Group K); and SEQ ID NOS:10, 11,12 & 13 (Group L). (N=6 for all groups). The error bars indicate ±1 standard deviation (S.D.).

Figure 13:
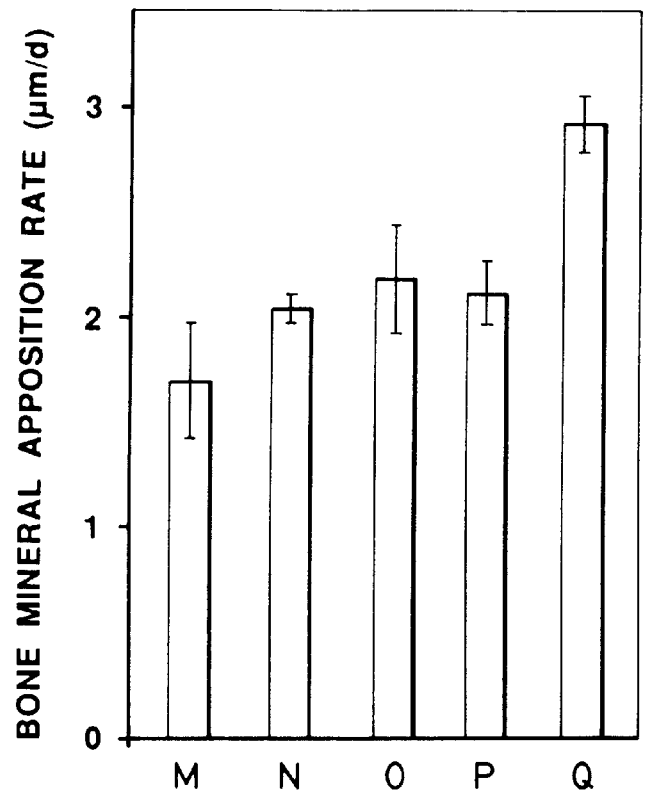

FIG. 13 graphically depicts the bone mineral apposition rate ($\mu$m per day) in rats injected with chemically synthesized polypeptide fragments SEQ ID NO:1 (Group N); SEQ ID NO:7 (Group O); SEQ ID NO:9 (Group P); and SEQ ID NO:24 (Group Q), and a control group (Group M). The error bars indicate ±1 standard deviation (S.D.).

Figure 14:
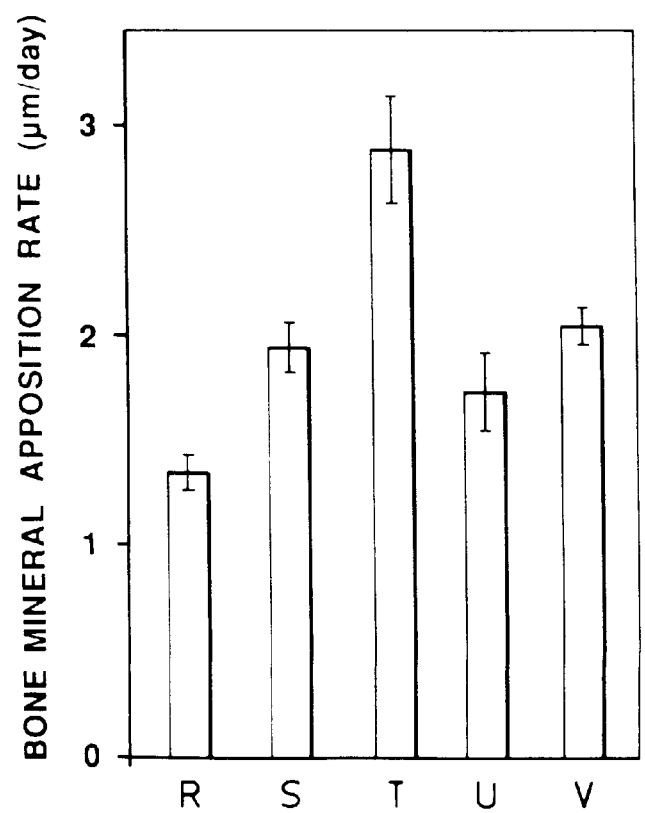

FIG. 14 graphically depicts the bone mineral apposition rate ($\mu$m per day) in rats injected with chemically synthesized polypeptide fragments SEQ ID NO:25 (Group S); SEQ ID NO:26 (Group T); SEQ ID NO:27 (Group U); SEQ ID NO:24 (Group V) and a control group (Group R). The error bars indicate ±1 standard deviation (S.D.).

FIG. 15 illustrates the amino sequences of the various polypeptides tested, active polypeptides being shown above the mid-line and sequences which were not found to stimulate bone growth being below the mid-line.

METHODOLOGY

The applicable methodology as described in the General Methodology section of international patent application No. PCT/CA 94/00144 was followed here.

TOXICITY EXPERIMENTS INVOLVING N-TERMINAL ACETYL CHEMICALLY SYNTHESIZED POLYPEPTIDE (SEQ ID NO: 2)

A miniosmotic pump (Alzet) was loaded with about 1.5 ml of the chemically synthesized peptide having an N-terminal acetyl group (SEQ ID NO:2) in 0.1% acetic acid so as to give a calculated daily delivery of about 25 $\mu$g per day. A pump was implanted under the subcutaneous fascia of the dorsal aspect of the left side of the thorax of five rats which had been parathyroidectomized seven days earlier. Five similarly parathyroidectomized rats received similar implants containing only 0.1% acetic acid. Five intact rats were also used as controls.

Twenty-eight days later 0.5 ml of an aqueous solution of tetracycline hydrochloride was injected intramuscularly into the right gluteus maximus of each of the implanted rats, as described previously. Another 48 hours later, a second injection of tetracycline hydrochloride solution was injected. The rats were sacrificed another 24 hours later.

Figure 1:
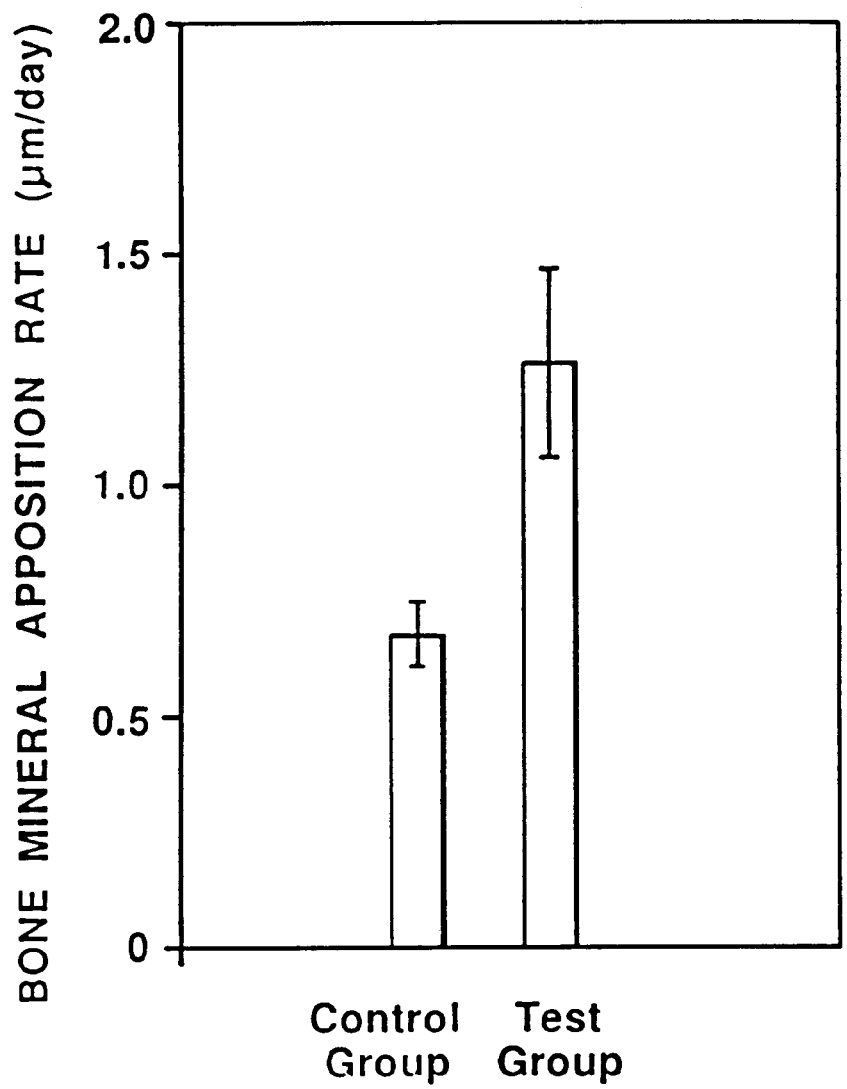

The bone mineral apposition rate was determined by examination of a cross-section of the lower metaphysis of the right femur of each of the ten rats which had been given implants. The results are summarized in Table One depicted graphically in FIG. 1.

TABLE ONE

Comparison of the Group Arithmetic Means Among Groups

|  | Test Group | Control Group |
|---|---|---|
| Mean | 1.27 $\mu$m/d | 0.67 $\mu$m/d |
| S.D. | 0.18 $\mu$m/d | 0.08 $\mu$m/d |
| N | 5 | 5 |
|  | t | d.f |
| Test Group vs Control Group | 7.14 | 8 |

Histological evaluation of selected tissues of the five rats of each of the groups indicated in Table One were carried out microscopically. No evidence of toxic lesions was found.

EXPERIMENTS INVOLVING OVARIECTOMIZED RATS AND THE NORMAL CHEMICALLY SYNTHESIZED POLYPEPTIDE (SEQ ID NO:1), ADMINISTRATION OVER A FOUR WEEK PERIOD

Ovariectomies were performed on six female Sprague-Dawley rats, each sedated with 1 mg of sodium barbiturate I.P. Sham operations were carried␣out a second group of six rats. The rats were given two weeks to recover from the operations.

The six ovariectomized rats were injected subcutaneously with 100 $\mu$l of a 0.1% acetic acid solution containing 100 $\mu$g of the chemically synthesized peptide (SEQ ID NO:1) every 24 hours for 28 days. On day 25, a tetracycline hydrochloride solution was injected intramuscularly into each rat so as to give 24 mg per Kg of body weight, as described previously. On day 27, a second dose of tetracycline hydrochloride was injected and the rats were sacrificed on the 28th day.

A second group of six ovariectomized rats, was similarly treated with a 0.1% acetic acid solution containing no peptide over the same 28 day period. A third group of six rats, each of which had undergone the sham operation, was similarly treated with a 0.1% acetic acid solution containing no peptide over the same 28 day period. A fourth group of six intact rats was similarly treated with a 0.1% acetic acid solution containing no peptide over the same 28 day period.

Postmortem blood was taken by cardiac puncture and serum frozen until analyzed. A full autopsy was performed on each rat. No ill effects were observed in the rats treated with the polypeptide.

Each of the right femurs was dissected out from its soft tissue, fixed for two days, and X-rays taken at 70 kV for 1 min., 2 min., and 3 min. The 3 minute exposures gave the most satisfactory results. The bone densities of the femurs from the second group of rats, the ovariectomized rats not treated with the peptide, showed a visibly lower bone density.

The right femur of each rat was decalcified separately. The decalcification fluid consisted of 10% formic acid (v/v) and 5% sodium citrate (w/v) at pH 3.0. Each bone was placed in 6 ml of the decalcification fluid. The fluid was replaced after 4 days, again after another 4 days, again after another 2 days, and again after another 3 days. After another 2 days, the decalcification fluid was removed and replaced by deionized water, and the sample agitated for 2 days. The water changed after two days and again after another day. After another day, all of the fluid samples for each rat were combined and the final volume of each adjusted to 50 ml with deionized water.

Figure 2:
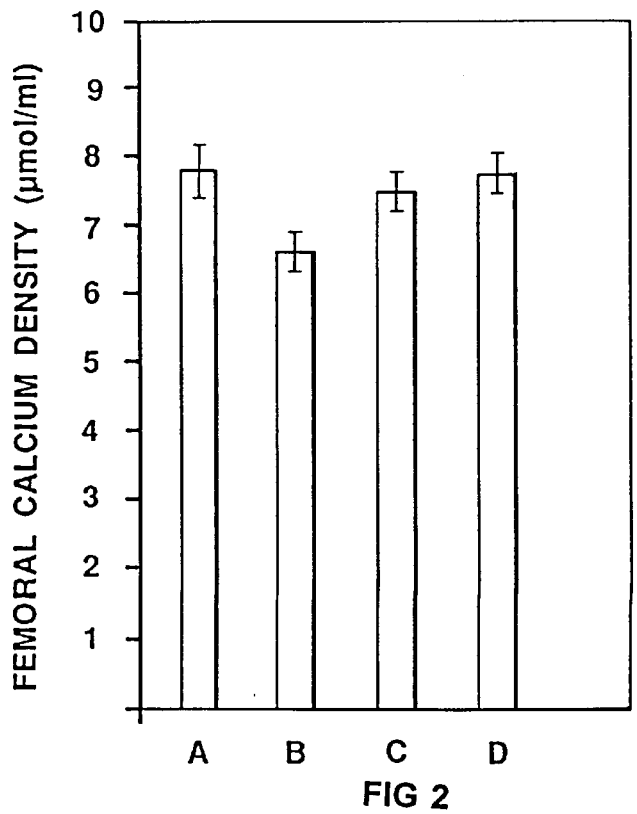
FIG. 2 graphically depicts right femoral bone calcium density of rats treated over a four week period. Group A rats were ovariectomized and injected daily with the chemically synthesized normal peptide (SEQ ID NO:1). Group B rats were ovariectomized and injected daily with control solution. Group C rats were subject to sham ovariectomization operations and injected daily with control solution. Group D were intact rats injected daily with control solution. The error bars indicate ±1 standard deviation (S.D.).

The volume of each right femur was determined by determining the volume of water displaced when the bone was immersed in water. The calcium concentration of each sample was determined according to standard methods and the calcium density of each bone calculated. The results are tabulated in Table Two and graphically depicted in FIG. 2. As can be seen, the bone calcium concentration measured for the ovariectomized rats treated with the peptide (SEQ ID NO:1) appears to be normal, while the calcium concentration of the untreated ovariectomized rats is depressed.

TABLE TWO

Right Femoral Calcium Concentration of Ovariectomized Rats

|  | Group A | Group B | Group C | Group D |
|---|---|---|---|---|
| Mean ($\mu$mol/ml) | 7.57 | 6.61 | 7.45 | 7.69 |
| N | 6 | 6 | 6 | 6 |
| S.D. | 0.38 | 0.29 | 0.28 | 0.31 |

| GROUP | t | d.f. | p |
|---|---|---|---|
| A vs B | 4.90 | 10 | <0.001 |
| A vs C | 0.62 | 10 | >0.5 |
| A vs D | 0.60 | 10 | >0.5 |
| B vs C | 5.08 | 10 | <0.001 |
| B vs D | 6.20 | 10 | <0.001 |
| C vs D | 1.40 | 10 | >0.1 |

Figure 3:
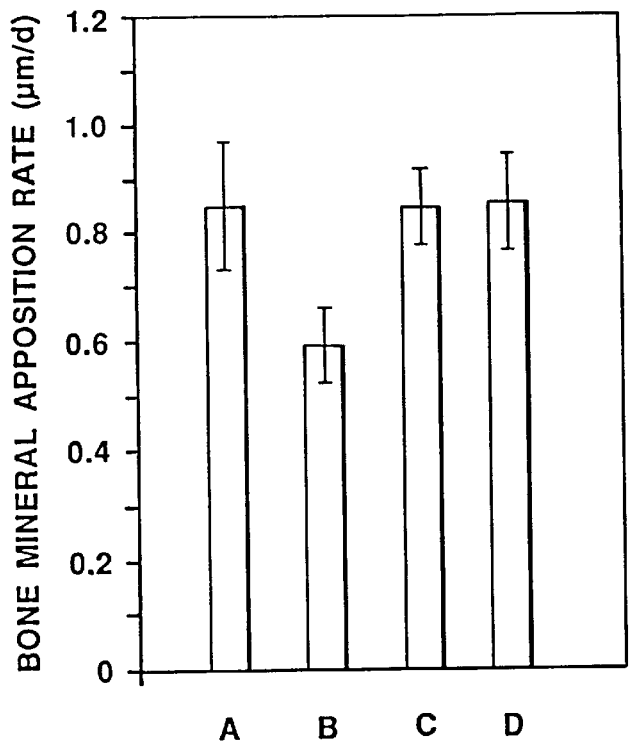
FIG. 3 graphically depicts the bone mineral apposition rate of rats as determined by tetracycline labeling after treatment as described in connection with FIG. 2. The error bars indicate ±1 standard deviation (S.D.).

The bone mineral apposition rate was determined, as described previously, by measurement of the lower metaphysis of the left femur. The results are tabulated in Table Three and graphically depicted in FIG. 3.

TABLE THREE

Bone Mineral Apposition Rates of Ovariectomized Rats

|  | Group A | Group B | Group C | Group D |
|---|---|---|---|---|
| Mean ($\mu$m/day) | 0.90 | 0.59 | 0.85 | 0.86 |
| N | 6 | 6 | 6 | 6 |
| S.D. | 0.12 | 0.07 | 0.07 | 0.09 |

| GROUP | t | d.f. | p |
|---|---|---|---|
| A vs B | 5.39 | 10 | <0.001 |
| A vs C | 0.87 | 10 | >0.5 |
| A vs D | 0.21 | 10 | >0.5 |
| B vs C | 6.29 | 10 | <0.001 |
| B vs D | 5.93 | 10 | <0.001 |
| C vs D | 0.21 | 10 | >0.5 |

EXPERIMENTS INVOLVING OVARIECTOMIZED RATS AND THE NORMAL CHEMICALLY SYNTHESIZED POLYPEPTIDE, ADMINISTRATION OVER AN EIGHT WEEK PERIOD

Eight weeks after ovariectomization, five ovariectomized rats were injected subcutaneously with 100 $\mu$l of a 0.1% acetic acid solution containing 100 $\mu$g of the chemically synthesized peptide in which the N-terminal amino group was modified with an acetyl group (SEQ ID NO:2). This was done every 24 hours for eight weeks. On day 54, a tetracycline hydrochloride solution was injected intramuscularly into the right gluteus maximus of each rat so as to give 24 mg per Kg of body weight, as described previously. On day 56, a second dose of tetracycline hydrochloride was injected and the rats were sacrificed on the 57th day.

A second group of seven ovariectomized rats, was similarly treated with a 0.1% acetic acid solution containing no peptide over the same period. A third group of five rats, each of which had undergone the sham operation, was similarly treated with a 0.1% acetic acid solution containing no peptide over the same period. A fourth group of five intact rats was similarly treated with a 0.1% acetic acid solution containing no peptide over the same 8 week period. Two rats of the second group became ill during the 8 week period and were sacrificed prematurely.

Postmortem blood was taken by cardiac puncture and serum frozen until analyzed. An autopsy was performed on each rat. No obvious pathology was observed in the rats except for surgical scars and atrophy of the uterus and vagina of ovariectomized rats.

Figure 4:
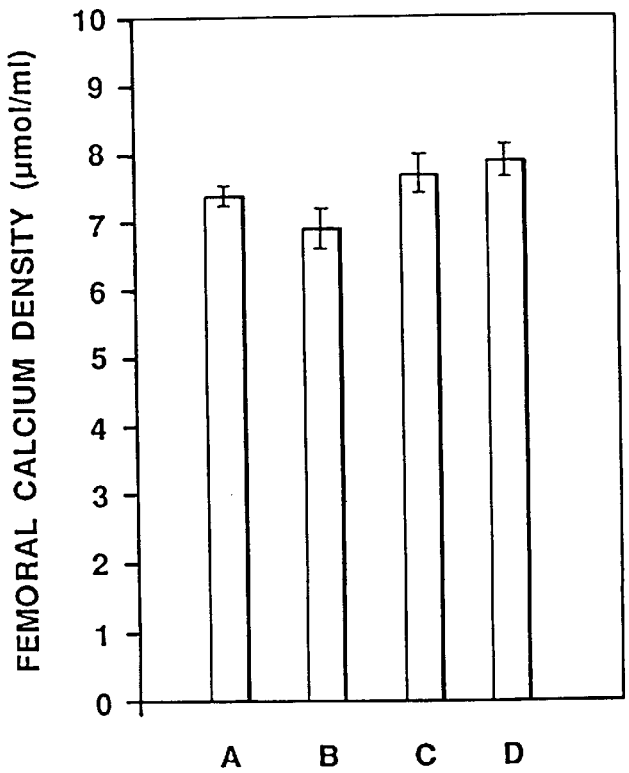
FIG. 4 graphically depicts femoral bone calcium concentration of rats treated over an eight week period. Group A rats were ovariectomized and injected daily with the chemically synthesized normal peptide (SEQ ID NO:1) beginning eight weeks after the operation. Group B rats were similarly ovariectomized and injected daily with control solution. Group C rats were subject to sham ovariectomization operations and injected daily with control solution. Group D were intact rats injected daily with control solution. The error bars indicate ±1 standard deviation (S.D.).

The right femurs were decalcified and calcium density determined as before. The results are presented in Table Four and FIG. 4.

TABLE FOUR

Right Femoral Calcium Concentration of Ovariectomized Rats

|  | Group A | Group B | Group C | Group D |
|---|---|---|---|---|
| Mean ($\mu$mol/ml) | 7.37 | 6.89 | 7.69 | 7.87 |
| N | 5 | 5 | 5 | 5 |
| S.D. | 0.15 | 0.32 | 0.30 | 0.24 |

| GROUP | t | d.f. | p |
|---|---|---|---|
| A vs B | 3.85 | 6 | <0.005 |
| A vs C | 1.17 | 6 | >0.2 |
| A vs D | 3.01 | 6 | <0.01 |
| B vs C | 4.03 | 6 | <0.005 |
| B vs D | 5.41 | 6 | <0.001 |
| C vs D | 1.60 | 6 | >0.1 |

SYNTHESIS OF ANTIBODIES TO CHEMICALLY SYNTHESIZED PROTEIN (SEQ ID NO: 1)

The chemically synthesized protein (SEQ ID NO:1) was coupled to KLH (keyhole limpet hemocyanin) with three different cross-linkers, as described below.

GLUTARALDEHYDE COUPLING

In 2.5 ml of a PBS solution made up of 2.7 mM KCl, 1.2 mM $KH_2PO_4$, 138 mM NaCl, 8.1 mM $Na_2HPO_4$, were diluted 5 mg of the peptide (SEQ ID NO:1) to obtain a final peptide concentration of 2 mg/ml. 10 mg of KLH were diluted in 5.0 ml PBS to obtain a final concentration of 2 mg/ml. To 1.25 ml of the KLH solution were added 1.25 ml of the peptide solution. Glutaraldehyde was added to a final concentration of 0.25%. The resultant solution was stirred for 1 hour at room temperature. After stirring, the solution was dialysed against 1 liter of PBS. The PBS was changed three times.

CARBODIIMIDE (EDC) COUPLING

Peptide and KLH solutions were prepared as described in the preceding section. To 1.25 ml KLH solution were added 1.25 ml peptide solution. To the resultant solution were added 2.5 mg of EDC. The solution was stirred constantly at room temperature for 4 hours and then dialysed against 1 liter of PBS. The PBS was changed three times.

M-MALEIMIDOBENZOYL-N-HYDROXYSUCCINIMIDE ESTER (MBS) COUPLING

To 500 μl of $H_2O$ were added 5 mg of the peptide and the pH was adjusted to 8.5 with NaOH, to obtain a final concentration of 10 mg/ml. Citraconic anhydride was diluted in $H_2O$ to a concentration of 10 mg/ml. 500 μl of the anhydride solution were added to the peptide solution 100 μl at a time with adjustment of the pH to 8.5 between each addition. The solution was then stirred constantly at room temperature for 1 hour. This was followed by the addition of 100 μl of 1M sodium phosphate buffer (pH 7.2) and then 900 μl of 100 mM sodium phosphate buffer (pH 7.2). Sulfo-MBS was diluted in $H_2O$ to a concentration of 25 mg/ml and 400 μl of this solution were added to the peptide solution to obtain an MBS concentration of about 5 mg/ml. This solution was stirred constantly at room temperature for 30 minutes. 6 μl of β-mercaptoethanol were added for a final β-mercaptoethanol concentration of 35 mM. The solution was stirred constantly at room temperature for 1 hour. KLH was dissolved in PBS at 3 mg/ml and 2.5 ml were added to the peptide solution. The solution was stirred constantly at room temperature for 3 hours and then dialysed against 1 liter of PBS, with three changes of the PBS. The final peptide concentration was about 1 mg/ml and the final KLH concentration was about 1.5 mg/ml.

ANTIBODY GENERATION

Rabbits were injected with the synthetic peptide solutions as follows. 250 μl each of the glutaraldehyde- and EDC-coupled peptide solutions were together mixed with 500 μl of Freund's adjuvant. This solution was injected intramuscularly into the rear legs of a rabbit, 500 μl per leg. The total amount of injected peptide was 0.5 mg. 500 μl of the synthetic peptide coupled to KLH with MBS were mixed with 500 μl of Freund's adjuvant. This solution was injected intramuscularly into the rear legs of another rabbit, 500 μl per leg. The total amount of injected peptide was 0.5 mg.

The synthetic peptide was loaded onto two lanes, 1.5 μg and 4 μg, of a gel (18% running, 5% stacking). The gel was blotted overnight at 30 V and blocked with 3% milk in PBS. The gel was incubated overnight with rabbit serum diluted 1:250 in 1% milk/PBS followed by incubation with goat anti-rabbit-alkaline phosphatase diluted 1:1000 for 1 hour. The gel was then developed with substrate. The synthetic peptide was seen by comasie blue staining. The peptide was detected by the second bleed of each rabbit and was not detected by the preimmune serum of either rabbit.

Interaction between immobilized peptide and serum antibodies was further studied through surface plasmon resonance using BlAcore™. The synthetic peptide was covalently immobilized on a dextran matrix by amine coupling. Rabbit serum of different dilutions were injected over the surface for five minutes and the amount of antibody bound to the immobilized peptide determined. The titer is defined as the last dilution of the serum giving a positive response, that is, greater than 50 Resonance Units. Using this approach, antibodies were found to be present in serum from both rabbits and the interaction can be blocked by preincubating the serum with the peptide. Antibodies in serum of the rabbits were found not to interact with an immobilized unrelated peptide.

EXPERIMENTS INVOLVING RATS AND ANTIBODIES TO THE CHEMICALLY SYNTHESIZED PEPTIDE

Antibody serum was prepared in 10 mM Tris.Cl at pH 7.4. Each of five rats received 100 μl of the solution by injection into the left gluteus maximus. Each rat of a second group of five rats was treated similarly, but with an additional injection of solution containing 45 μg of the polypeptide (SEQ ID NO:1) into the right gluteus maximus. Each rat of a third group of five rats received an injection of 100 μl of 10 mM Tris.Cl at pH 7.0.

Each of the fifteen rats was then injected as before with tetracycline hydrochloride, in the amount of 24 mg per Kg of body weight. A second dose of tetracycline hydrochloride was injected about 48 hours later. The rats were sacrificed after about another 24 hours.

Figure 5:
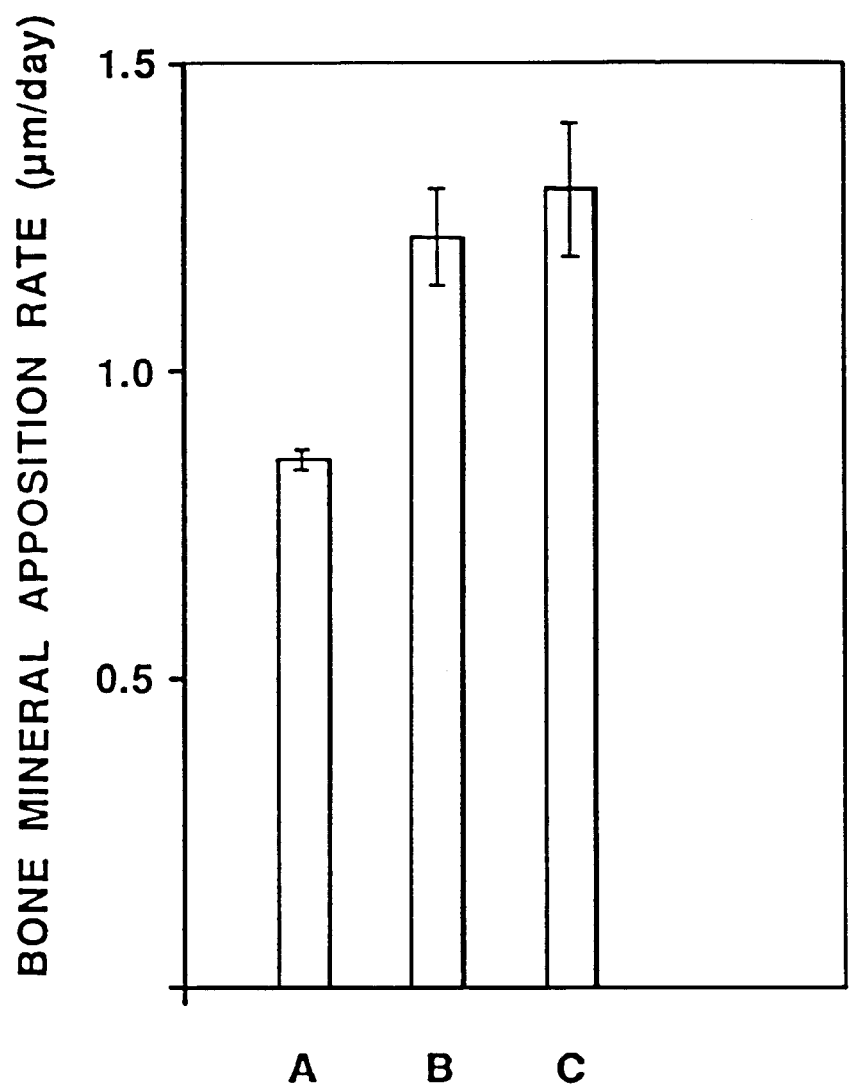
FIG. 5 graphically depicts the bone mineral apposition rate of intact rats as determined by tetracycline labeling. Group A rats were treated with rabbit antibodies to the chemically synthesized normal polypeptide (SEQ ID NO:1).

The bone mineral apposition rate was determined by measurements, described above, of the lower right femoral metaphysis. The results are given in Table Five and FIG. 5.

TABLE FIVE

Bone Mineral Apposition Rates in Rats Injected with Antibody to the Chemically Synthesized Peptide

|  | Group A | Group B | Group C |
|---|---|---|---|
| Mean (μm/day) | 0.86 | 1.22 | 1.30 |
| S.D. | 0.02 | 0.08 | 0.11 |
| N | 5 | 5 | 5 |

|  | t | d.f | p |
|---|---|---|---|
| Group A vs Group B | 8.06 | 8 | >0.2 |
| Group A vs Group C | 7.57 | 8 | <0.001 |
| Group B vs Group C | 1.24 | 8 | >0.2 |

Methodology and products can be thus be developed using antibody to the polypeptide for use in detecting the polypeptide with which the antibody binds. For example, antibody can be linked to or conjugated with any of several well known reporter systems set up to indicate positively binding of the polypeptide to the antibody. Well known reporter systems include radioimmuno assays (RIAs) or immunoradiometric assays (IRMAs). Alternatively, an enzyme-linked immunosorbent assay (ELISA) would have in common with RIAs and IRMAs a relatively high degree of sensitivity, but would generally not rely upon the use of radioisotopes. A visually detectable substance may be produced or at least one detectable in a spectrophotometer. An assay relying upon fluorescence of a substance bound by the enzyme being assayed could be used. It will be appreciated that there are a number of reporter systems which may be used, according to the present invention, to detect the presence of a particular polypeptide. With standardized sample collection and treatment, polypeptide presence above a threshold amount in blood serum could well be determined.

Such a method based on antigenic response to the chemically synthesized human polypeptide (SEQ ID NO:1) could be developed and variants of the polypeptide obtained, as described above for amino acid substitution, deletion and addition, (and conjugates) could then be pre-screened as potential bone stimulating factors. Those that react positively with the antibody to the already known peptide could then be tested for bone stimulatory effects in vivo using the system described herein for rats, for example.

Such an antibody-linked reporter system could be used in a method for determining whether blood serum of a subject contains a deficient amount of the polypeptide. Given a normal threshold concentration of such a polypeptide in blood serum of a given type of subject, test kits could thus be developed.

EXPERIMENTS INVOLVING CHEMICALLY SYNTHESIZED HUMAN POLYPEPTIDE CONTAINING CYSTEINE→ALANINE SUBSTITUTION

A modified sequence (SEQ ID NO:3) of the chemically synthesized peptide (SEQ ID NO:1) obtained by substitution of the cysteine residue at position 13 by alanine was prepared by standard chemical procedures. An alanine residue is sterically similar to a reduced cysteine residue while rendering the polypeptide incapable of spontaneous dimerization. A tricine SDS electrophoretic gel of the modified and unmodified (normal) peptides is shown in FIG. 6.

Experiments were carried out on three groups of six rats weighing between 295 and 320 g. A1 mg per ml solution of the modified peptide (SEQ ID NO:3) was prepared in 0.1% acetic acid. A 1 mg per ml solution of the normal peptide (SEQ ID NO:1) was prepared in 0.1% acetic acid. Each rat of a first of the groups had subcutaneously injected into its right thigh 0.1 ml of the modified peptide solution. Similarly, each rat of the second group was injected with 0.1 ml of the normal peptide solution. Each rat of the third group, the control group, was injected with 0.1 ml of 0.1% acetic acid solution. Immediately following these injections, each rat was injected intramuscularly with 24 mg per Kg body weight of tetracycline hydrochloride dissolved in 0.5 ml of water. A second dose of tetracycline hydrochloride was administered 48 hours later. The animals were sacrificed 24 hours after the second dose by $CO_2$ narcosis. The lower metaphysis of the right femur was dissected out and fixed in a 10% aqueous solution of formaldehyde buffered at pH 7.2 by acetate buffer. Bone sections were prepared for measurement as described above.

The results are tabulated in Table Six and graphically depicted in FIG. 7. As can be seen, the bone apposition rate for rats injected with the modified polypeptide is significantly greater than that for those of the control group but below the bone apposition rate shown for the rats injected with the normal peptide.

TABLE SIX

Comparison of the Group Arithmetic Means Among Groups Injected with Modified Peptide, Unmodified Peptide and Control

|  | Group A | Group B | Control Group |
|---|---|---|---|
| Mean | 1.67 μm/d | 1.35 μm/d | 1.02 μm/d |
| S.D. | 0.11 μm/d | 0.16 μm/d | 0.010 μm/d |
| N | 6 | 6 | 6 |

|  | t | d.f | p |
|---|---|---|---|
| Group A vs Control (Group C) | 12.2 | 10 | <0.001 |
| Group B vs Control (Group C) | 4.69 | 10 | <0.001 |
| Group A vs Group B | 3.97 | 10 | <0.005 |

EXPERIMENTS INVOLVING ACTIVE FRAGMENTS OF THE 36-AMINO ACID HUMAN POLYPEPTIDE

Polypeptides having the amino acid sequences identified as SEQ ID NOS:4, 5, 6, 7, 8 and 9 were synthesized according to well known chemical procedures.

Sprague-Dawley rats were used as test animals to determine bone mineral apposition rate, as described above. Male rats having weights between 280 and 380 g were subject to subcutaneous injection after one week of acclimatization. Each animal was injected with 200 μl of a 0.1% acetic acid test solution, solutions having been prepared at concentrations to obtain a dosage of about 25 nmol of polypeptide per animal. Each test dose was immediately followed by intramuscular injection of 24 mg per Kg of body weight of tetracycline hydrochloride. A second injection of tetracycline was made 48 hours later.

Control Group: 0.1% acetic acid solution

Group A: SEQ ID NO:1:
Gly Ile Gly Lys Arg Thr Asn Glu His Thr Ala Asp Cys Lys Ile Lys Pro Asn Thr Leu His Lys Lys Ala Ala Glu Thr Leu Met Val Leu Asp Gin Asn Gln Pro Group E: SEQ ID NO:4:
Gly Ile Gly Lys Arg Thr Asn Glu His Thr Ala Asp Cys Lys Ile Lys Pro Asn Thr Leu His Lys Lys Ala Ala Glu Thr Leu Met Val Group D: SEQ ID NO:5:
Gly Ile Gly Lys Arg Thr Asn Glu His Thr Ala Asp Cys Lys Ile Lys Pro Asn Thr Leu His Lys Lys Ala Ala Group C: SEQ ID NO:6:
Gly Ile Gly Lys Arg Thr Asn Glu His Thr Ala Asp Cys Lys Ile Lys Pro Asn Thr Leu Group B: SEQ ID NO:7:
Gly Ile Gly Lys Arg Thr Asn Glu His Thr Ala Asp Cys Lys Ile In a similar but separate set of experiments, bone mineral apposition rates were tested using the following chemically synthesized polypeptides:

Group F: SEQ ID NO:8:
Gly Ile Gly Lys Arg Thr Asn Glu His Thr Ala Asp Cys Lys

Group G: SEQ ID NO:9:
Arg Thr Asn Glu His Thr Ala Asp Cys Lys

Bone mineral apposition rates were determined by measurements of the lower metaphysis of the right femur, as described previously. Results obtained in the two sets of experiments are summarized in Tables Seven and Eight and graphically depicted in FIGS. 8 and 9. As can be seen, all of the polypeptides tested had a positive effect on bone apposition rate, i.e, displayed bone stimulatory activity.

TABLE SEVEN

Comparison of the Group Arithmetic Means Among First Groups Injected with Active Variants

|  | Group A | Group B | Group C | Group D | Group E | Control |
|---|---|---|---|---|---|---|
| Mean | 1.4 | 1.41 | 1.37 | 1.35 | 1.31 | 1.03 |
| S.D. | 0.05 | 0.08 | 0.09 | 0.1 | 0.06 | 0.06 |
| N | 6 | 6 | 6 | 6 | 6 | 6 |

|  | t | d.f. | p |
|---|---|---|---|
| Group A vs Control | 5.18 | 10 | <0.001 |
| Group B vs Control | 9.67 | 10 | <0.001 |
| Group C vs Control | 7.64 | 10 | <0.001 |
| Group D vs Control | 6.92 | 10 | <0.001 |
| Group E vs Control | 7.99 | 10 | <0.001 |
| Group A vs Group B | 0.14 | 10 | >0.5 |
| Group A vs Group C | 0.4 | 10 | >0.5 |
| Group A vs Group D | 0.66 | 10 | >0.5 |
| Group A vs Group E | 1.3 | 10 | >0.2 |
| Group B vs Group C | 0.82 | 10 | >0.4 |
| Group B vs Group D | 1.19 | 10 | >0.2 |
| Group B vs Group E | 2.49 | 10 | <0.05 |

TABLE EIGHT

Comparison of the Group Arithmetic Means Among Second Groups Injected with Active Variants

|  | Group F | Group G | Control Group |
|---|---|---|---|
| Mean | 2.09 μm/d | 2.83 μm/d | 1.63 μm/d |
| S.D. | 0.34 μm/d | 0.19 μm/d | 0.13 μm/d |
| N | 4 | 3 | 4 |

TABLE EIGHT-continued

Comparison of the Group Arithmetic Means Among Second Groups Injected with Active Variants

|  | t | d.f | p |
|---|---|---|---|
| Group F vs Control | 6 | | 0.047 |
| Group G vs Control | 5 | | 0.0002 |
| Group F vs Group G | 5 | | 0.215 |

BONE CALCIUM CONTENT EXPERIMENTS INVOLVING SEQ ID NO:7

A further set of experiments was conducted using the polypeptide identified as SEQ ID NO:7 to determine the effect of the polypeptide on bone calcium content when administered to rats.

Ovariectomies were performed on rats as described above. A 0.1% acetic acid solution containing 25 nmoles of the polypeptide was administered subcutaneously to each rat each day for the duration of the experiment. One group of rats was treated for 12 weeks beginning 100 days after ovariectomization. Another group of rats was treated for eight weeks beginning eight weeks after ovariectomization. Rats were sacrificed at the end of the treatment period and dissected and post mortem assessment of bone mineral content was carried out.

The lumbar spines L1–L4 were cleaned with a power nylon brush to remove the attached muscle. They were placed ventral side down under 3 cm of distilled water in a polypropylene container and scanned by a dual energy x-ray absorptometer (DEXA), Hologic 100, to determine the calcium content in grams. The right femur of each rat was also dissected out intact and cleared of the attached muscles with a power nylon brush. It was scanned dorsal side down under 3 cm of distilled water by DEXA. Four regions of the femur were scanned, as indicated in FIGS. 10 and 11: A, proximal end; B, diaphysis; C, distal end; and D, neck. The bone mineral (i.e., calcium) content in grams was estimated in the four zones of the femur based on absorption and using an internal standard of the machine.

Results are tabulated in Tables Nine to Eighteen.

TABLE NINE

Comparison of Group Arithmetic Means Among Groups Injected with Polypeptide SEQ ID NO:7 Administered over 100 Days to Ovariectomized Rats-Bone Mineral Content Measured in Proximal End of Femur

|  | Control | A-Ovariectomized (no polypeptide) | B-Ovariectomized (with polypeptide) |
|---|---|---|---|
| Mean (g.) | 0.1503 | 0.1351 | 0.1411 |
| S.D. | 0.0159 | 0.0105 | 0.0155 |
| N | 14 | 14 | 11 |

|  | t | d.f | p |
|---|---|---|---|
| Control vs A | 2.9772 | 26 | <0.025 |
| Control vs B | 1.44 | 23 | N.S. |
| Group A vs Group B | 1.1634 | 23 | N.S. |

TABLE TEN

Comparison of Group Arithmetic Means Among Groups Injected with Polypeptide SEQ ID NO:7 Administered over 56 Days to Ovariectomized Rats-Bone Mineral Content Measured in Proximal End of Femur

|  | Control | Sham | A-Ovariectomized (no polypeptide) | B-Ovariectomized (with polypeptide) |
|---|---|---|---|---|
| Mean (g.) | 0.1451 | 0.1387 | 0.1368 | 0.1328 |
| S.D. | 0.0183 | 0.0166 | 0.028 | 0.0141 |
| N | 5 | 5 | 6 | 6 |

|  | t | d.f | p |
|---|---|---|---|
| Control vs Sham | 0.7372 | 8 | N.S. |
| Control vs A | 0.6261 | 9 | N.S. |
| Control vs B | 1.6223 | 9 | N.S. |
| Sham vs A | 0.133 | 9 | N.S. |
| Sham vs B | 1.6229 | 9 | N.S. |
| Group A vs B | 0.3116 | 10 | N.S. |

TABLE ELEVEN

Comparison of Group Arithmetic Means Among Groups Injected with Polypeptide SEQ ID NO:7 Administered over 100 Days to Ovariectomized Rats-Bone Mineral Content Measured in Spine (L1–L4)

|  | Control | A-Ovariectomized (no polypeptide) | B-Ovariectomized (with polypeptide) |
|---|---|---|---|
| Mean (g) | 0.5437 | 0.4364 | 0.4758 |
| S.D. | 0.0161 | 0.0089 | 0.0188 |
| N | 14 | 14 | 10 |

|  | t | d.f | p |
|---|---|---|---|
| Control vs A | 5.8384 | 26 | <0.001 |
| Control vs B | 2.7434 | 22 | <0.0025 |
| Group A vs Group B | 2.0756 | 22 | 0.05 |

TABLE TWELVE

Comparison of Group Arithmetic Means Among Groups Injected with Polypeptide SEQ ID NO:7 Administered over 56 Days to Ovariectomized Rats-Bone Mineral Content Measured in Spine (L1–L4)

|  | Control | Sham | A-Ovariectomized (no polypeptide) | B-Ovariectomized (with polypeptide) |
|---|---|---|---|---|
| Mean (g.) | 0.5542 | 0.5321 | 0.4322 | 0.4606 |
| S.D. | 0.0275 | 0.0172 | 0.0226 | 0.0234 |
| N | 5 | 5 | 6 | 6 |

|  | t | d.f | p |
|---|---|---|---|
| Control vs Sham | 0.6805 | 8 | N.S. |
| Control vs A | 4.4196 | 9 | <0.005 |
| Control vs B | 3.1042 | 9 | <0.025 |
| Sham vs A | 2.8382 | 9 | <0.025 |
| Sham vs B | 1.9951 | 9 | N.S. |
| Group A vs B | 0.8759 | 10 | N.S. |

TABLE THIRTEEN

Comparison of Group Arithmetic Means Among Groups Injected with Polypeptide SEQ ID NO:7 Administered over 100 Days to Ovariectomized Rats-Bone Mineral Content Measured in Femoral Diaphysis

|  | A-Ovariectomized | B-Ovariectomized |
|---|---|---|

TABLE THIRTEEN-continued

Comparison of Group Arithmetic Means Among Groups Injected with Polypeptide SEQ ID NO:7 Administered over 100 Days to Ovariectomized Rats-Bone Mineral Content Measured in Femoral Diaphysis

|  | Control | (no polypeptide) | (with polypeptide) |
|---|---|---|---|
| Mean (g.) | 0.2258 | 0.2146 | 0.2347 |
| S.D. | 0.0261 | 0.0106 | 0.0215 |
| N | 14 | 14 | 11 |

|  | t | d.f | p |
|---|---|---|---|
| Control vs A | 0.8301 | 26 | N.S. |
| Control vs B | 0.9078 | 23 | N.S. |
| Group A vs Group B | 2.3079 | 23 | <0.05 |

TABLE FOURTEEN

Comparison of Group Arithmetic Means Among Groups Injected with Polypeptide SEQ ID NO:7 Administered over 56 Days to Ovariectomized Rats-Bone Mineral Content Measured in Femoral Diaphysis

|  | Control | Sham | A-Ovariectomized (no polypeptide) | B-Ovariectomized (with polypeptide) |
|---|---|---|---|---|
| Mean (g.) | 0.2179 | 0.1918 | 0.1716 | 0.2091 |
| S.D. | 0.0156 | 0.0162 | 0.0272 | 0.0121 |
| N | 5 | 5 | 6 | 6 |

|  | t | d.f | p |
|---|---|---|---|
| Control vs Sham | 2.259 | 8 | <0.05 |
| Control vs A | 3.3549 | 9 | <0.025 |
| Control vs B | 1.9209 | 9 | N.S. |
| Sham vs A | 1.4571 | 9 | N.S. |
| Sham vs B | 1.1778 | 9 | N.S. |
| Group A vs B | 2.4926 | 10 | <0.05 |

TABLE FIFTEEN

Comparison of Group Arithmetic Means Among Groups Injected with Polypeptide SEQ ID NO:7 Administered over 100 Days to Ovariectomized Rats-Bone Mineral Content Measured in Distal End of Femur

|  | Control | A-Ovariectomized (no polypeptide) | B-Ovariectomized (with polypeptide) |
|---|---|---|---|
| Mean (g.) | 0.1597 | 0.1396 | 0.1424 |
| S.D. | 0.0185 | 0.0068 | 0.0132 |
| N | 14 | 14 | 11 |

|  | t | d.f | p |
|---|---|---|---|
| Control vs A | 3.8255 | 26 | <0.001 |
| Control vs B | 2.616 | 23 | <0.025 |
| Group A vs Group B | 0.6984 | 23 | N.S. |

TABLE SIXTEEN

Comparison of Group Arithmetic Means Among Groups Injected with Polypeptide SEQ ID NO:7 Administered over 56 Days to Ovariectomized Rats-Bone Mineral Content Measured in Distal End of Femur

|  | Control | Sham | A-Ovariectomized (no polypeptide) | B-Ovariectomized (with polypeptide) |
|---|---|---|---|---|
| Mean (g.) | 0.1826 | 0.154 | 0.1304 | 0.1347 |
| S.D. | 0.0122 | 0.0118 | 0.0094 | 0.0039 |
| N | 5 | 5 | 6 | 6 |

|  | t | d.f | p |
|---|---|---|---|
| Control vs Sham | 3.7549 | 8 | <0.025 |
| Control vs A | 8.0183 | 9 | <0.001 |
| Control vs B | 9.1462 | 9 | <0.001 |
| Sham vs A | 3.7046 | 9 | <0.005 |
| Sham vs B | 3.8149 | 9 | <0.005 |
| Group A vs B | 1.0274 | 10 | N.S. |

TABLE SEVENTEEN

Comparison of Group Arithmetic Means Among Groups Injected with Polypeptide SEQ ID NO:7 Administered over 100 Days to Ovariectomized Rats-Bone Mineral Content Measured in Femoral Neck

|  | Control | A-Ovariectomized (no polypeptide) | B-Ovariectomized (with polypeptide) |
|---|---|---|---|
| Mean (g.) | 0.0334 | 0.0303 | 0.0351 |
| S.D. | 0.0049 | 0.004 | 0.0031 |
| N | 14 | 14 | 10 |

|  | t | d.f | p |
|---|---|---|---|
| Control vs A | 1.3978 | 26 | N.S. |
| Control vs B | 1.0326 | 21 | N.S. |
| Group A vs Group B | 2.259 | 21 | P < 0.005 |

TABLE EIGHTEEN

Comparison of Group Arithmetic Means Among Groups Injected with Polypeptide SEQ ID NO:7 Administered over 56 Days to Ovariectomized Rats-Bone Mineral Content Measured in Femoral Neck

|  | Control | Sham | A-Ovariectomized (no polypeptide) | B-Ovariectomized (with polypeptide) |
|---|---|---|---|---|
| Mean (g.) | 0.0277 | 0.0255 | 0.0202 | 0.0274 |
| S.D. | 0.002 | 0.0038 | 0.0028 | 0.0013 |
| N | 5 | 5 | 6 | 6 |

|  | t | d.f | p |
|---|---|---|---|
| Control vs Sham | 1.1534 | 8 | N.S. |
| Control vs A | 4.9809 | 9 | <0.001 |
| Control vs B | 0.3342 | 9 | N.S. |
| Sham vs A | 2.662 | 9 | <0.05 |
| Sham vs B | 1.1462 | 9 | N.S. |
| Group A vs B | 5.6713 | 10 | <0.005 |

As can be seen from the tabulated data, the increase in in vivo calcium bone content is most obvious in the femoral neck and femoral diaphysis, implying that the effect of the administered peptide can be site specific, possibly being greater at skeletal sites under mechanical stress.

EXPERIMENTS INVOLVING OTHER FRAGMENTS OF THE 36-AMINO ACID HUMAN POLYPEPTIDE

Polypeptide fragments of the normal polypeptide (SEQ ID NO:1) were also synthesized and tested for bone stimulatory activity as with the C-terminus fragments.

Control Group: 0.1% acetic acid

Group H: SEQ ID NO:1:

Gly Ile Gly Lys Arg Thr Asn Glu His Thr Ala Asp Cys Lys
   Ile Lys Pro Asn Thr Leu His Lys Lys Ala Ala Glu Thr Leu
   Met Val Leu Asp Gln Asn Gln Pro

Group I: SEQ ID NO:16:

Arg Thr Asn Glu His Thr Ala Asp Cys Lys Ile

Group J: SEQ ID NO:15:

Arg Thr Asn Glu His Thr Ala Asp Cys Lys Ile Lys Pro Asn
   Thr Leu His Lys Lys Ala Ala Glu Thr Leu Met Val Leu
   Asp Gln Asn

Group K: SEQ ID NO:14:

Thr Ala Asp Cys Lys Ile Lys Pro Asn Thr Leu His Lys Lys
   Ala Ala Glu Thr Leu Met Val Leu Asp

Group L: SEQ ID NOS: 10,11,12 & 13 (mixture):

Leu His Lys Lys Ala Ala Glu Thr Leu Met Val Leu Asp Gln
   Asn Gln Leu His Lys Lys Ala Ala Glu Thr Leu Met Val
   Leu Asp Gln Asn Leu His Lys Lys Ala Ala Glu Thr Leu
   Met Val Leu Asp Gln Leu His Lys Lys Ala Ala Glu Thr
   Leu Met Val Leu Asp

Bone mineral apposition rates were again determined by measurement of the lower metaphysis of the right femur. Results obtained are summarized in Table Nineteen and graphically depicted in FIG. 12. As can be seen in FIG. 12, none of the non-N-terminus variants identified as SEQ ID NO: 10, 11, 12, 13, 14, 15 or 16 was found to increase the bone apposition rate with respect to the control.

TABLE NINETEEN

Summary of the Group Arithmetic Means for Bone Apposition Rates of Rats Injected with Non-N-terminus Variants

|  | Group H | Group I | Group J | Group K | Group L | Control |
|---|---|---|---|---|---|---|
| Mean ($\mu$m/day) | 1.5 | 1.02 | 0.92 | 0.92 | 0.98 | 1.02 |
| S.D. | 0.09 | 0.12 | 0.09 | 0.04 | 0.09 | 0.06 |
| N | 6 | 6 | 6 | 6 | 6 | 6 |

A polypeptide having the ten amino acid sequence of SEQ ID NO:9, but protected at both ends was synthesized and tested for bone stimulatory activity in comparison to polypeptides identified as SEQ ID NOS: 1, 7 and 9. The protected polypeptide was acetylated at the amino terminus and amidated at the carboxy terminus and is identified herein as SEQ ID NO:24. Results obtained according to experimental procedures described above, using about 125 nmoles of polypeptide per Kg of body weight of animal are presented in Table Twenty and FIG. 13.

TABLE TWENTY

Comparison of the Mean Bone Apposition Rates Among Rats Treated with SEQ ID NOs: 1, 7, 9 and 24

|  | SEQ ID NO:1 | SEQ ID NO:7 | SEQ ID NO:9 | SEQ ID NO:24 | Control |
|---|---|---|---|---|---|
| Mean ($\mu$m/day) | 2.03 | 2.18 | 2.11 | 2.72 | 1.7 |
| S.D. | 0.1 | 0.26 | 0.18 | 0.15 | 0.28 |
| N | 6 | 6 | 6 | 6 | 6 |

|  | t | d.f. | p |
|---|---|---|---|
| SEQ ID NO:1 vs Control | >2.6 | 10 | <0.025 |
| SEQ ID NO:7 vs Control | −3.03 | 10 | <0.003 |
| SEQ ID NO:9 vs Control | −2.96 | 10 | <0.006 |
| SEQ ID NO:24 vs Control | −7.73 | 10 | <0.00 |
| SEQ ID NO:1 vs 7 | −1.28 | 10 | >0.2 |
| SEQ ID NO:1 vs 9 | −0.898 | 10 | >0.3 |
| SEQ ID NO: vs 24 | −4.42 | 10 | <0.002 |

TABLE TWENTY-continued

Comparison of the Mean Bone Apposition Rates Among Rats Treated with SEQ ID NOs: 1, 7, 9 and 24

| SEQ ID NO:7 vs 9 | 0.548 | 10 | >0.5 |
|---|---|---|---|
| SEQ ID NO:7 vs 24 | −4.42 | 10 | <0.002 |
| SEQ ID NO:9 vs 24 | −6.38 | 10 | <0.00 |

There are literature reports that the presence of histidine and cysteine residues in polypeptides [Int. J. Peptide Protein Res. 45, 1995, 547,553]. The following analogues of the polypeptide identified as SEQ ID NO:9 were synthesized:

SEQ ID NO:25:

$CH_3CO$—Arg Thr Asn Glu His Thr Ala Glu Cys Lys—$NH_2$

SEQ ID NO:26:

$CH_3CO$—Arg Thr Gln Glu His Thr Ala Glu Cys Lys—$NH_2$

SEQ ID NO:27:

$CH_3CO$—Arg Thr Gln Glu His Thr Ala Asp Cys Lys—$NH_2$

Each of the polypeptides having the sequences identified as SEQ ID NO: 7 and 24 was dissolved in 5 mM acetic acid to a final concentration of 1 mg/ml and incubated at 37° C. The peptide compositions were analyzed weekly by capillary electrophoresis on a P/ACE 6000 system (Beckman) using 50 mM sodium phosphate pH 2.5 as the running buffer on a 57 cm long×75 $\mu$m internal diameter capillary. The incubated peptide (20 $\mu$l) was diluted with 80 $\mu$l of running buffer, placed in a 500 $\mu$l vial prior to injection onto the P/ACE using pressure for 20 seconds. Following electrophoresis of the incubated peptide at 30 kV for 15 min a second run was carried out using freshly dissolved peptide as a control.

Analytical results indicated that each of the polypeptides tested underwent modification. Mass spectroscopic results (not shown) indicated that both peptides were breaking down to smaller fragments, i.e., undergoing proteolysis.

Each of the polypeptides was dissolved in 20 mM sodium phosphate pH 3.0, 20 mM ammonium acetate pH 4.0, 20 mM ammonium acetate pH 5.0, 20 mM MES pH 6.0, 20 mM sodium phosphate pH 7.0, 20 mM sodium phosphate pH 7.5, 20 mM sodium phosphate pH 8.0, 20 mM ammonium acetate pH 8.5 or 20 mM ammonium acetate pH 9.5 to a final concentration of 1 mg/ml. The peptide was incubated at 37° C. and the peptide assayed weekly by separation on P/ACE as described above. Some samples were separated by RP-HPLC and the isolated peaks subjected to mass spectroscopic analysis.

Analytic results indicated that the polypeptide identified as SEQ ID NO: 24 was most stable at a pH near 4.5. When incubated above pH 6.0, the peptide dimerized. The peptide degraded when incubated below pH 4.0. The polypeptide having the amino acid sequence identified as SEQ ID NO:7 had a similar stability profile.

The protected polypeptide identified as SEQ ID NO:24 was dissolved in 20 mM or 250 mM ammonium acetate pH 4.5 to a final concentration of 1 mg/ml. In some experiments the buffer was supplemented with 20 mM EDTA. The peptide solution was then incubated at −70° C., −20° C., 4° C. or room temperature (22° C). Samples were assayed weekly by electrophoresis on the P/ACE as described above and/or by RP-HPLC.

Analytical results indicated that the peptide is very stable as a powder and when dissolved in pH 4.5 buffer. Modification of the peptide incubated at room temperature was observed after 7 days as a peak eluting before the intact peptide on the RP-HPLC chromatogram. The peptide modification was not altered by addition of 20 mM EDTA or by incubation in 250 mM ammonium acetate. Dissolved peptide incubated at 4° C., −20° C. or −70° C. were unchanged as compared with dry peptide stored at −70° C. After 14 days of incubation at room temperature, the HPLC profile included the two peaks observed at day 7, plus an additional peak with a retention time greater than intact peptide. While the dissolved peptide incubated at room temperature continued to become modified with increasing time, it was apparent that it was most stable in the lower salt buffer with the addition of 20 mM EDTA. Incubation of peptide at all other temperatures did not significantly alter the HPLC profile as compared with dry peptide stored at −70° C. up to 28 days.

The stability of each of the polypeptides having the amino acid sequences identified as SEQ ID NOS: 25, 26 and 27 was tested as described above.

The polypeptide having SEQ ID NO: 27 was found to be unstable at all pHs tested when incubated at 37° C. for 3 days. Numerous additional peaks were observed on its electropherogram. The polypeptide having SEQ ID NO:25 was stable at pH 2.5–3.0 for 20 days. The polypeptide having SEQ ID NO:26 was found to be stable at pH 2.5–3.0 when incubated at 37° C.

In general, polypeptides having amino acid sequences identified as SEQ ID NOS: 7 and 24 degraded over time when dissolved in dilute acids. These peptides were found to be most stable when dissolved in pH 4.5 buffer. Analogues, SEQ ID NOS: 25 and 26 were found to be more stable than SEQ ID NOS: 7 or 24, while SEQ ID NO:27 was found to be significantly less stable.

Polypeptide having the amino acid sequences identified as SEQ ID NOS: 25, 26 and 27 were tested for bone stimulatory activity in comparison to the polypeptide identified as SEQ ID NOS: 24. Results obtained according to experimental procedures described above are presented in Table Twenty-One and FIG. 14.

TABLE TWENTY-ONE

Comparison of the Mean Bone Apposition Rates Among Rats Treated with SEQ ID NOs: 24, 25, 26 and 27

|  | SEQ ID NO:24 | SEQ ID NO:25 | SEQ ID NO:26 | SEQ ID NO:27 | Control |
|---|---|---|---|---|---|
| Mean ($\mu$m/day) | 2.04 | 1.94 | 2.88 | 1.72 | 1.36 |
| S.D. | 0.14 | 0.23 | 0.47 | 0.33 | 0.14 |
| N | 4 | 4 | 4 | 4 | 4 |

A summary of the results obtained with respect to particular polypeptide sequences tested is provided in FIG. 15.

As can be seen, the polypeptide identified as SEQ ID NO:24 (and the corresponding unprotected polypeptide, SEQ ID NO:9) has a sequence of 10 amino acids contained in the 36 amino acid sequence of the polypeptide identified as SEQ ID NO:1. Thus, in vivo bone stimulatory activity can be retained with a polypeptide in which as little as 28% of the amino acid sequence of SEQ ID NO:1 is conserved. In particular, the protected version of the 10-amino acid polypeptide sequence, SEQ ID NO:24, has a bone stimulatory effect which exceeds that of either SEQ ID NO:1 or the 10-amino acid unprotected version, SEQ ID NO:9.

Further, As can be seen the polypeptide identified as SEQ ID NO:26 (and the corresponding unprotected polypeptide, SEQ ID NO:29) has a sequence of 10 amino acids, only eight of which are identical to those contained in the 36 amino acid sequence of the polypeptide identified as SEQ ID NO:1. This indicates that in vivo bone stimulatory activity can be retained in a polypeptide in which as little as 22% of the amino acid sequence of SEQ ID NO:1 is conserved. On a molar basis, the protected sequence (SEQ ID NO:26) has been found, at least under the conditions of the foregoing experiments, have an even more potent effect than that of SEQ ID NO:24.

Likewise, the polypeptide identified as SEQ ID NO:25 (and the corresponding unprotected polypeptide, SEQ ID NO:28) has a sequence of 10 amino acids, only nine of which are identical to those contained in the 36 amino acid sequence of the polypeptide identified as SEQ ID NO:1. This indicates that in vivo bone stimulatory activity can be retained in a polypeptide in which as little as 25% of the amino acid sequence of SEQ ID NO:1 is conserved. On a molar basis, the protected sequence (SEQ ID NO:25) has been found under the conditions of the experiments described above to have a comparable bone stimulatory effect to that of SEQ ID NO:24.

The polypeptide identified as SEQ ID NO:27 (and the corresponding unprotected polypeptide, SEQ ID NO:30) has a sequence of 10 amino acids, only nine of which are the same as those contained in SEQ ID NO:1. The protected version of this polypeptide was found to have the bone stimulatory effect also, but it was not as great as that of SEQ ID NO:26.

As indicated in the experiments described above, the polypeptides vary from each other according to the conditions to which the polypeptides are exposed. It is generally desirable that an active polypeptide not be degraded to an inactive or less active moiety when stored or during administration. Information about the stability of an active fragment is useful in formulating preparations for storage and administration. Stability information might also be useful in selecting a fragment that is longer lived once administered to an individual.

Of course it is known to those skilled in the art that polypeptides which provide similar activity are generally related by having the same or similar three-dimensional portion(s) which interacts with another agent, such as a receptor with which the polypeptide binds in some way. This is why it is possible to have several polypeptides that are related to each other that display similar bone-stimulating activity.

The present invention provides a synthetic polypeptide having in vivo bone stimulatory activity in mammals and which increases calcium density or content in bones of mammals, having an amino acid sequence which is at least about 19% conserved in relation to the amino acid sequence identified as SEQ ID NO:1 and having at least one amino acid deleted therefrom, or a homologue thereof. In the context of this invention, a peptide containing an amino acid sequence that can be aligned with that of SEQ ID NO:1 such that at least about 30% of individual amino acid residues of the original sequence are present in the peptide is said to be about 30% conserved with the amino acid sequence identified as SEQ ID NO:1, allowing for homologous substitutions and a limited number of insertions or deletions between aligned sequences. An amino acid sequence having seven out of the 36 amino acid residues of SEQ ID NO:1 in aligned sequence would be 19% conserved. An amino acid sequence having eight out of the 36 amino acid residues of SEQ ID NO:1 in aligned sequence would be 22% conserved, such as is the case of SEQ ID NOS:26 and 29. An amino acid sequence having nine out of the 36 amino acid residues of SEQ ID NO:1 in aligned sequence would be 25% conserved, as for SEQ ID NOS:25, 27, 28 and 30. An amino acid sequence having ten out of the 36 amino acid residues of SEQ ID NO:1 in aligned sequence is 28% conserved, as for SEQ ID NOS:9 and 24.

Described in a slightly different way, a polypeptide of the present invention is an amino acid sequence corresponding to SEQ ID NO:1 with (a) one amino acid to 4 amino acids deleted from the N-terminus of SEQ ID NO:1, (b) one to 22 amino acids deleted from the C-terminus of SEQ ID NO:1, or both (a) and (b); or a functionally equivalent homologue. It may be found possible to delete 5 or 6 or more amino acids from the N-terminus or to delete more than 22 amino acids from the C-terminus of SEQ ID NO:1.

In another sense, the polypeptide of the present invention can be described as a polypeptide exhibiting bone stimulatory activity in mammals, the polypeptide having the sequence identified as SEQ ID NO:1, SEQ ID NO:3, SEQ ID NO:4, SEQ ID NO:5, SEQ ID NO:4, SEQ ID NO:6, SEQ ID NO:7, SEQ ID NO:8, or SEQ ID NO:9; analogues thereof wherein the amino acids in the sequence may be substituted, deleted or added, so long as the bone stimulatory activity in mammals derived from the three dimensional structure of the sequence is preserved; and conjugates of each of the polypeptides or analogues thereof, wherein if the polypeptide sequence has that identified as SEQ ID NO:1, then there is at least one amino acid deleted therefrom.

A polypeptide of the present invention would include such a sequence which sequence would have a molecular weight in the range of from about 1000 to 4000. It is to be understood however that the sequence might be added to by conjugation or other technique, which could increase the molecular weight of the overall compound beyond 4000.

It will also be understood, without the intention of being limited thereby, that a variety of substitutions of amino acids is possible while "preserving" the three-dimensional structure responsible for the bone stimulatory effect of the polypeptides disclosed herein. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, cysteine, asparagine and glutamine could possibly be made. This being said, the linkage of the peptides together by the disulfide bridge appears to be of some importance, and so the lone cysteine residue should probably be held intact and other amino acids capable of forming a disulfide linkage not be substituted elsewhere in the sequence, although as seen above a successful cys→ala substitution was effected (SEQ ID NO:3). Substitutions among the charged acidic amino acids, aspartic acid and glutamic acid, can be made, as shown above, and substitutions among the charged basic amino acids, lysine and arginine are also likely to be possible. Substitutions can be made alone or in combination. These sorts of substitutions and interchanges are well known to those skilled in the art. U.S. Pat. Nos. 5,487,983 and 5,512,548, for instance, describes other possible substitutions including substitutions involving amino acids not encoded by the gene. Other substitutions might well be possible.

The importance of the N-terminus portion of the sequence is evident from the results described herein. The polypeptides (SEQ ID NOS:9, 24, 25, 26, 27, 28, 29 and 30) having amino acids 5 to 14 of SEQ ID NO:1 displays bone stimulatory activity while polypeptides lacking the first nine N-terminus amino acids, but having amino acids 10 to 32 (SEQ ID NO:14) or amino acids 20 to 35 (SEQ ID NO:10) do not display bone stimulatory activity. It may be that it is possible to delete more amino acids from either end of the polypeptide identified as SEQ ID NO:9 while retaining the three-dimensional configuration of the subsequence of the polypeptide responsible for bone stimulatory activity. Internal deletions, although they might be possible to some limited extent, should be few. Of particular note, is the polypeptide having the sequence identified as SEQ ID NO:16, which differs by only one amino acid residue from the amino acid sequence identified as SEQ ID NO: 9. The former does not display activity while the latter does display bone stimulatory activity. It is possible using the experimental methods disclosed herein to distinguish between sequences which do and do not stimulate bone growth and which do and do not increase calcium bone content.

It should still be possible for minor additions of amino acids to be made at the ends of the sequence and symmetrical or nearly symmetrical additions to the carboxy and amino terminals are likely to be possible. Internal additions, although likely to be possible to some limited extent, should be few.

Of the above-listed modifications to the sequence, terminal additions, deletions or substitutions are most likely to be most useful, as such a modification can serve a variety of functions: an identifying group as for use in a radioimmunoassay; or a linking group, as examples.

As with the normal peptide (SEQ ID NO:1), an active subsequence containing a cysteine residue (i.e., SEQ ID Nos: 4, 5, 6, 7, 8 or 9) can spontaneously dimerize and exist in the dimeric form, at least under certain conditions.

A further advantage may be obtained through chimeric forms of the protein, as known in the art. A DNA sequence encoding the entire protein, or a portion of the protein, could thus be linked with a sequence coding for the C-terminal portion of *E. coli* β-galactosidase to produce a fusion protein, for example. An expression system for human respiratory syncytial virus glycoproteins F and G is described in U.S. Pat. No. 5,288,630, issued Feb. 22, 1994, and references cited therein, for example.

A polypeptide of the present invention would usually be synthetic, whether prepared by techniques of conventional "chemistry" or by recombinant techniques. Here, a polypeptide so produced is referred to as being substantially pure or biochemically pure when it is generally free of polypeptides or proteins with which it would occur if found directly in nature, as in blood serum from an animal, for example.

Nucleic acid (DNA) sequences coding for the active portions of the normal polypeptide would be as follows:
SEQ ID NO:17 (corresponding to SEQ ID NO:4):
GGG ATC GGA AAA CGA ACA AAT GAA CAT ACG GCA GAT TGT AAA ATT AM CCG AAC ACC TTG CAT AAA AAA GCT GCA GAG ACT TTA ATG GTC
SEQ ID NO:18 (corresponding to SEQ ID NO:5):
GGG ATC GGA AAA CGA ACA AAT GAA CAT ACG GCA GAT TGT AAA ATT AAA CCG AAC ACC TTG CAT AAA AAA GCT GCA
SEQ ID NO:19 (corresponding to SEQ ID NO:6):
GGG ATC GGA MA CGA ACA AAT GAA CAT ACG GCA GAT TGT AAA ATT AAA CCG MC ACC TTG
SEQ ID NO:20 (corresponding to SEQ ID NO:7):

GGG ATC GGA AAA CGA ACA AAT GAA CAT ACG GCA GAT TGT AAA ATT
SEQ ID NO:21 (corresponding to SEQ ID NO:8):
GGG ATC GGA AAA CGA ACA AAT GAA CAT ACG GCA GAT TGT AAA
SEQ ID NO:22 (corresponding to SEQ ID NO:9):
CGA ACA AAT GAA CAT ACG GCA GAT TGT AAA Hypothetical coding sequences for polypeptides based on SEQ ID NO:1 but having amino acid residues substituted therefor, are:
SEQ ID NO:31 (corresponding to SEQ ID NO:28):
CGA ACA MT GAA CAT ACG GCA GAA TGT AAA
SEQ ID NO:32 (corresponding to SEQ ID NO:29):
CGA ACA CAA GAA CAT ACG GCA GAA TGT AAA
SEQ ID NO:33 (corresponding to SEQ ID NO:30):
CGA ACA CAA GAA CAT ACG GCA GAT TGT AAA Accordingly, a vector incorporating such a DNA sequence could be constructed for use in synthesizing a polypeptide, as described previously, and particularly in international patent application No. PCT/CA 94/00144. The DNA sequence coding for the polypeptide identified as SEQ ID NO:1 is given as SEQ ID NO:23 in the sequence listing of this specification.

A DNA sequence or fragment of the present invention may be any fragment that contains a nucleotide sequence which encodes a polypeptide of the present invention. In addition to any of the above coding sequences, the DNA fragment can have an appropriate promoter and an SD sequence (or a suitable ribosome binding site) at its 5'-end, and if necessary, a nucleotide sequence containing a translation initiation codon at the 5'-end and a nucleotide sequence containing a termination codon at the 3'-end.

As known to those skilled in the art, the genetic code is "degenerate". A nucleotide in a gene sequence can thus be replaced by another nucleotide in accordance with the degeneracy of a particular codon (coding triplet), without changing the amino acid sequence of the polypeptide coded for by the gene. A DNA fragment of the present invention can thus be derived from any of the above sequences (and DNA sequences corresponding to substituted polypeptide or other analogues not explicitly illustrated), and such replacement might be done in such a way that the resulting codon(s) shows a high utilization frequency in a specific host cell when producing a polypeptide of the present invention using genetic engineering techniques.

As used herein, "protected" terminal amino group refers to a terminal amino group (N-terminus) coupled with any of various amino4terminal protecting groups that can be employed in peptide synthesis. Examples of suitable groups include acyl protecting groups, for example, formyl, acetyl, benzoyl, trifluoroacetyl, succinyl, and methoxysuccinyl; aromatic urethane protecting groups, for example benzyloxycarbonyl; and aliphatic urethane protecting groups, for example t-butoxycarbonyl or adamantyloxycarbonyl (Gross and Mienhofer, eds., The *Peptides*, vol 3, pp. 3 to 88 (Academic Press, New York, 1981)).

As used herein, "protected" terminal carboxyl group refers to a terminal carboxyl group (C-terminus) coupled with any of various carboxy-terminal protecting groups. As will be readily apparent to a person skilled in the art, suitable groups include t-butyl, benzyl or other acceptable groups linked to the terminal carboxyl group through an ester or ether bond.

Compounds within the scope of this invention can be synthesized chemically by means well known in the art such, for example, solid phase peptide synthesis. The synthesis is commenced from the carboxy-terminal end of the peptide using an α-amino protected amino acid. t-Butyloxycarbonyl (Boc) protective groups, or other suitable protective groups, can be used (Stewart et al., "Solid-Phase Peptide Synthesis," W. H. Freeman Co., San Francisco (1969); Merrifield, *J. Am. Chem. Soc*. 85:2149–2154 (1963); Vale etal., *Science* 213, 1394–1397 (1981), and Marke etal. *J. Am Chem. Sci*. 103, 3178 (1981)). Synthetic methods are also described in "Principles of Peptide Synthesis" M. Bodansky Ed. (Spring-Verlag 1984). These and other methods of peptide synthesis are also exemplified by U.S. Pat. Nos. 3,862,925, 3,842,067, 3,972,859, 4,105,602, 4,683,291, 4,244,946 and 4,305,872.

Compounds may also be synthesized using manual or automatic techniques, for example, an Applied BioSystems 430A Peptide Synthesizer (Foster City, Calif.) or a Biosearch SAM 11 automatic peptide synthesizer (Biosearch, Inc., San Rafael, Calif.).

Compounds of the present invention and compositions containing them find use in numerous therapeutic and prophylactic applications in the prevention and treatment of bone reduction related to a disease. Compounds can thus be used as treatments to promote bone growth, in the treatment of osteoporosis, for example, by any suitable route. The preferred routes are suitable for delivery of polypeptide-type compounds to the bloodstream of a subject, bearing in mind proper storage and handling conditions required for polypeptides such as those described herein.

Thus the present invention also provides compositions containing an effective amount of compounds of the present invention, including the nontoxic addition salts, amides and esters thereof, which may, alone, serve to provide the treatment benefits described above. Such compositions can also be provided together with physiologically tolerable liquid, gel or solid diluents, adjuvants and excipients.

In the above examples involving subsequences of about 125 nmol of polypeptide per kg of bodyweight of animal was used per administration. In practice, particularly as human subjects are concerned, the daily dosage may well be between 0.01 and 300 mg or more per kg of bodyweight. More preferably, the dosage would be in the neighborhood of from about 0.1 to about 30 mg per kg of bodyweight. It may be that the preferred frequency of administration would be greater or less than once per day, depending upon the route of administration, convenience, and the variation of effectiveness of treatment with frequency of and amount used per administration. The dosage administered also depends on the subject and to which effect such administration is to give. The dosage of any one or more of the compounds will depend on many factors including the specific compound or combination of compounds being utilized, the mode of administration, and the mammal being treated. Dosages of a particular compound or combination of compounds can be determined using conventional considerations; for example, by customary comparison of the differential activities of the subject compounds and that of a known agent, that is, by means of an appropriate pharmacological protocol in which, for example, bone density of subjects is measured over time.

Pharmaceutical preparations include any of the compounds prepared as an injectable solution, including an injectable solution prepared just prior to use, for promoting bone growth and/or treatment of osteoporosis. An injectable can be either a liquid solution or suspension; solid forms suitable for solution in, or suspension in, liquid prior to injection may also be prepared. The preparation may also be emulsified. The active polypeptide is often mixed with diluents and excipients which are physiologically tolerable and compatible with the polypeptide. Suitable diluents and excipients are, for example, water, saline, dextrose, glycerol, or the like, and combinations thereof. In addition, if desired, the compositions can contain minor amounts of auxiliary substances such as wetting or emulsifying agents, stabilizing or pH buffering agents, and the like.

Pharmaceutical preparations include the employment of the compounds in admixture with conventional excipients, that is, pharmaceutically acceptable organic or inorganic carrier substances which do not deleteriously react with the compounds, and which possibly enhance the storage and handling stability of the compounds. The preparative procedure may include the sterilization of the pharmaceutical preparations. The compounds may be mixed with auxiliary agents such as lubricants, preservatives, stabilizers, salts for influencing osmotic pressure, etc., which do not react deleteriously with the compounds.

The compositions are conventionally administered parenterally, by injection, for example either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills capsules, sustained release formulations, or powders, and contain 10%–95% of active ingredient, preferably 25%–70%. These oral formulations include formulations designed to protect the peptide until it can be absorbed.

The peptide compounds may be formulated into the compositions as neutral or salt forms. Pharmaceutically acceptable non-toxic salts include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The compounds of the invention can be homopolymerized to themselves (i.e., (peptide)$_n$) or, heteropolymerized to one another. The compounds can also be conjugated to biocompatible polymeric compounds, such as BIOPOL™ (WR Grace & Co.-Conn.).

If prepared using recombinant techniques, a DNA sequence encoding a desired polypeptide of the present invention is synthesized using standard automated techniques, or the coding sequences or portions thereof are retrieved from cDNA or genomic libraries. This DNA is ligated into suitable expression vectors and these vectors are transformed into appropriate hosts. A variety of expression vector/host cell systems can be used, including both pro- caryotic and eukaryotic culture systems.

Procaryotes most frequently are represented by various strains of *E. coli*. However, other microbial strains may also be used, such as bacilli, for example *bacillus subtilis*, various species of Pseudomonas, or other bacterial strains. In such procaryotic systems, plasmid vectors which contain replication origins, and control sequences derived from a species compatible with the host are used. For example, *E. coli* is typically transformed using derivatives of pBR322, a plasmid derived from an *E. coli* species (Bolivar et al., (1977) *Gene* 2:95. Commonly used procaryotic control sequences, which are defined herein to include promoters for transcription initiation, optionally with an operator, along with ribosome binding site sequences, include such commonly used promoters as the beta-lactamase (penicillinase), lactose (lnc) promoter systems (Chang et al., (1977) *Nature* 198:1056), the tryptophan (trp) promoters system (Goeddel et al., (1990) *Nucleic Acids Res* 8:4057), and the lambda-derived $P_L$ promoter and N-gene ribosome binding site (Shimatake et al., (1981) *Nature* 292:128). However, any available promoter system compatible with procaryotes can be used.

The expression systems useful in the eukaryotic systems of the invention comprise promoters derived from appropriate eukaryotic genes. A class of promoters useful in yeast, for example, include promoters for synthesis of glycolytic enzymes, including alcohol dehydrogenase promoters, glyceraldehyde-3-phosphate dehydrogenase promoter (Holland & Holland, (1980) *J Biol Chem* 25:2596), alpha-factor promoter (Bitter et al., (1984) *Proc Natl Acad Sci* 81:5330), the gal promoter (Johnston & David, (1984) *Mol Cell Biol* 4:1440) those for 3-phosphoglycerate kinase (Hitzeman et al., (1980) *J. Biol Chem* 256:1385) or the Leu2 gene obtained from YEp13 (Broach, J., et al., (1978) *Gene* 8:121).

Suitable mammalian promoters include the early and late promoters from SV40 (Fiers et al., (1978) *Nature* 273:113) or other viral promoters such as those derived from polyoma, adenovirus II, bovine papilloma virus or avian sarcoma viruses. Suitable viral and mammalian enhancers are cited above. In the event plant cells are used as an expression system, the nopaline synthesis promoter is appropriate (Depicker, A., et al., (1982) *J Mol Appl Gen* 1:56).

The expression systems are included on replication vectors or are caused to integrate into the chromosome of a recombinant host. For systems wherein the vectors include a replication system, these may be low or high copy number, usually having copy numbers of fewer than about 1000, although in certain situations, runaway vectors may be employed. Whether provided on a vector intended for integration or in a replication system, the sequence encoding a polypeptide of the invention may be ligated in tandem with an amplifying gene such as dihydrofolate reductase, metallothioneins, thymidine kinase, or the like. In procaryotic systems, both the amplifying gene and the target gene can be under the regulation of the same transcriptional and translational regulatory regions.

Usually, the vector will include a marker which allows for selection of host cells containing the expression system; the nature of these markers depends on the host and is understood in the art. In addition to required regulators such as promoters, additional sequences such as enhancers can also be employed to enhance the level of transcription. If the polypeptide is to be secreted, an upstream sequence encoding signal peptides such as those described in U.S. Pat. Nos. 4,336,336; 4,338,397; and 4,546,082 may be employed. The signal sequence is enzymatically cleaved as the polypeptide product is secreted.

Depending on the host cell used, transformation is done using standard techniques appropriate to such cells. The calcium treatment employing calcium chloride, as described by Cohen, S. N., (1972) *Proc Natl Acad Sci USA* 69:2110; or the RbCl method described in Maniatis et al., *Molecular Cloning: A Laboratory Manual* (1982) Cold Spring Harbor Press, p. 254 is used for procaryotes or other cells which contain substantial cell wall barriers. Infection with *Agrobacterium tumefaciens* (Shaw, C. H., (1938) et al., *Gene* 23:315) is used for certain plant cells. For mammalian cells without such cell walls, the calcium phosphate precipitation method of Graham and van der Eb, (1978) *Virology* 52:2:546 is preferred. Transformations into yeast are carried out, for example, according to the method of Van Solingen, P., et al., (1977) *J Bacter* 130:946; and Hsiao, C.L., et al., (1979) *Proc Natl Acad Sci USA* 76:3829.

In general, after construction of a suitable expression system, the system is transfected into the appropriate host and successful transformants are selected by markers contained on the expression vectors. Successfully transformed colonies are then cultured in order to produce the desired polypeptide. It is sometimes preferred that a promoter which can be controlled by regulating conditions in the environment be used so that the cells can be grown under conditions where the gene encoding the desired polypeptide of the invention is not expressed, and then production of the polypeptide induced by appropriate manipulation of conditions. For example, if the trp promoter is used in *E. coli*, the cells are grown in the presence of tryptophan and expression is then induced by diminution of tryptophan concentration or by addition of a tryptophan analogue such as indolylacetic acid. If the gene is under control of the PL promoter, the cells are grown at relatively low temperature, such as at about 35° C., to a suitable cell density, and the temperature is then elevated to activate this promoter. If produced in bacterial hosts as a mature intracellular polypeptide, the N-terminal methionine may or may not be cleaved. In mammalian systems, for example, the use of the metallothionein promoter permits induction by addition of heavy metals or glucocorticoids. This protocol is preferred to prevent premature accumulation of the polypeptide which might be harmful to the growth of the cell.

The polypeptide can be produced intracellularly, or in secreted form by construction of vectors in which the peptide is preceded by a signal peptide workable in the appropriate host.

The polypeptide is recovered from the medium or from the cells using suitable techniques generally known in the art, and purified by, for example, ion exchange chromatography, ammonium sulfate precipitation, gel permeation chromatography, and so forth.

It will of course be understood, that antibodies to any of the polypeptides disclosed herein could be generated, as described in connection with the "normal" polypeptide (SEQ ID NO:1). Methodology and products can be developed using an antibody to a polypeptide for use in detecting the polypeptide with which the antibody binds. Methodology and products can be developed using an antibody to a polypeptide for use in detecting the polypeptide with which the antibody binds.

For example, an antibody can be linked to or conjugated with a reporter system which is set up to indicate positively binding of the polypeptide to the antibody. Well known reporter systems include radioimmuno assays (RIAs) or immunoradiometric assays (IRMAs). Alternatively, an enzyme-linked immunosorbent assay (ELISA) would have in common with RIAs and IRMAs a relatively high degree of sensitivity, but would generally not rely upon the use of radioisotopes. A visually detectable substance may be produced or at least one detectable in a spectrophotometer. An assay relying upon fluroescence of a substance bound by the enzyme being assayed could be used. It will be appreciated that there are a number of reporter systems which may be used, according to the present invention, to detect the presence of a particular polypeptide. With standardized sample collection and treatment, polypeptide presence above a threshold amount in blood serum could well be determined.

Such an antibody-linked reporter system could be used in a method for determining whether blood serum of a subject contains a deficient amount of the polypeptide. Given a normal threshold concentration of such a polypeptide in blood serum of a given type of subject, test kits could thus be developed.

What is claimed is:

1. A synthetic polypeptide having the amino acid sequence identified as SEQ ID NO:1 wherein at least one amino acid has been deleted therefrom provided that amino acids 5 to 14 of SEQ ID NO:1 are not deleted, or a substituted variant thereof in which (i) a non-polar, aliphatic neutral amino acid has been substituted for another non-polar, aliphatic neutral amino acid, (ii) a polar aliphatic neutral amino acid has been substituted for another polar aliphatic neutral amino acid, (iii) a charged acidic amino acid has been substituted for another charged acidic amino acid, (iv) a charged basic amino acid has been substituted for another charged basic amino acid, (v) cysteine has been substituted by alanine, or (vi) a combination of substitutions (i)–(v) has been made, whereby said synthetic polypeptide has bone stimulatory activity in animals and which increases mineral content in bones of animals.

2. A synthetic polypeptide of claim 1 wherein at least 6 amino acids have been deleted from SEQ ID NO:1.

3. A synthetic polypeptide of claim 1 wherein at least 16 amino acids have been deleted from SEQ ID NO:1.

4. A synthetic polypeptide of claim 1 wherein at least 21 amino acids have been deleted from SEQ ID NO:1.

5. A synthetic polypeptide of claim 1 wherein 26 amino acids have been deleted from SEQ ID NO:1.

6. A chimeric bone stimulating factor comprising a synthetic polypeptide of claim 1.

7. A method of increasing bone growth in a mammal comprising administering to said mammal an amount of the synthetic polypeptide according to claim 1 effective to increase bone growth in said mammal.

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 36 amino acids
      (B) TYPE: amino acid
      (C) STRANDEDNESS: single
      (D) TOPOLOGY: linear (xi) SEQUENCE DESCRIPTION: SEQ ID NO:1:

```
Gly Ile Gly Lys Arg Thr Asn Glu His Thr Ala Asp Cys Lys Ile Lys
1               5                   10                  15

Pro Asn Thr Leu His Lys Lys Ala Ala Glu Thr Leu Met Val Leu Asp
            20                  25                  30

Gln Asn Gln Pro
        35
```

(2) INFORMATION FOR SEQ ID NO:2:

(i) SEQUENCE CHARACTERISTICS:
　　　　(A) LENGTH: 36 amino acids
　　　　(B) TYPE: amino acid
　　　　(C) STRANDEDNESS: single
　　　　(D) TOPOLOGY: linear (ix) FEATURE:
　　　　(A) NAME/KEY: Modified-site
　　　　(B) LOCATION: 1
　　　　(D) OTHER INFORMATION: /product= "Other"
　　　　　　　/note= "The Xaa at position 1 is N-acetyl glycine."

(xi) SEQUENCE DESCRIPTION: SEQ ID NO:2:

Xaa Ile Gly Lys Arg Thr Asn Glu His Thr Ala Asp Cys Lys Ile Lys
1               5                   10                  15

Pro Asn Thr Leu His Lys Lys Ala Ala Glu Thr Leu Met Val Leu Asp
            20                  25                  30

Gln Asn Gln Pro
        35

(2) INFORMATION FOR SEQ ID NO:3:

(i) SEQUENCE CHARACTERISTICS:
　　　　(A) LENGTH: 36 amino acids
　　　　(B) TYPE: amino acid
　　　　(C) STRANDEDNESS: single
　　　　(D) TOPOLOGY: linear (xi) SEQUENCE DESCRIPTION: SEQ ID NO:3:

Gly Ile Gly Lys Arg Thr Asn Glu His Thr Ala Asp Ala Lys Ile Lys
1               5                   10                  15

Pro Asn Thr Leu His Lys Lys Ala Ala Glu Thr Leu Met Val Leu Asp
            20                  25                  30

Gln Asn Gln Pro
        35

(2) INFORMATION FOR SEQ ID NO:4:

(i) SEQUENCE CHARACTERISTICS:
　　　　(A) LENGTH: 30 amino acids
　　　　(B) TYPE: amino acid
　　　　(C) STRANDEDNESS: single
　　　　(D) TOPOLOGY: linear (xi) SEQUENCE DESCRIPTION: SEQ ID NO:4:

Gly Ile Gly Lys Arg Thr Asn Glu His Thr Ala Asp Cys Lys Ile Lys
1               5                   10                  15

Pro Asn Thr Leu His Lys Lys Ala Ala Glu Thr Leu Met Val
            20                  25                  30

(2) INFORMATION FOR SEQ ID NO:5:

(i) SEQUENCE CHARACTERISTICS:
　　　　(A) LENGTH: 25 amino acids
　　　　(B) TYPE: amino acid
　　　　(C) STRANDEDNESS: single
　　　　(D) TOPOLOGY: linear (xi) SEQUENCE DESCRIPTION: SEQ ID NO:5:

Gly Ile Gly Lys Arg Thr Asn Glu His Thr Ala Asp Cys Lys Ile Lys
1               5                   10                  15

Pro Asn Thr Leu His Lys Lys Ala Ala
            20                  25

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:6:

```
Gly Ile Gly Lys Arg Thr Asn Glu His Thr Ala Asp Cys Lys Ile Lys
1               5                   10                  15
Pro Asn Thr Leu
            20
```

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:7:

```
Gly Ile Gly Lys Arg Thr Asn Glu His Thr Ala Asp Cys Lys Ile
1               5                   10                  15
```

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:8:

```
Gly Ile Gly Lys Arg Thr Asn Glu His Thr Ala Asp Cys Lys
1               5                   10
```

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:9:

```
Arg Thr Asn Glu His Thr Ala Asp Cys Lys
1               5                   10
```

(2) INFORMATION FOR SEQ ID NO:10:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:10:

```
Leu His Lys Lys Ala Ala Glu Thr Leu Met Val Leu Asp Gln Asn Gln
1               5                   10                  15
```

(2) INFORMATION FOR SEQ ID NO:11:

(i) SEQUENCE CHARACTERISTICS:
        (A) LENGTH: 15 amino acids
        (B) TYPE: amino acid (C) STRANDEDNESS: single
            (D) TOPOLOGY: linear (xi) SEQUENCE DESCRIPTION: SEQ ID NO:11:

Leu His Lys Lys Ala Ala Glu Thr Leu Met Val Leu Asp Gln Asn
1               5                  10                  15

(2) INFORMATION FOR SEQ ID NO:12:

(i) SEQUENCE CHARACTERISTICS:
            (A) LENGTH: 14 amino acids
            (B) TYPE: amino acid
            (C) STRANDEDNESS: single
            (D) TOPOLOGY: linear (xi) SEQUENCE DESCRIPTION: SEQ ID NO:12:

Leu His Lys Lys Ala Ala Glu Thr Leu Met Val Leu Asp Gln
1               5                  10

(2) INFORMATION FOR SEQ ID NO:13:

(i) SEQUENCE CHARACTERISTICS:
            (A) LENGTH: 13 amino acids
            (B) TYPE: amino acid
            (C) STRANDEDNESS: single
            (D) TOPOLOGY: linear (xi) SEQUENCE DESCRIPTION: SEQ ID NO:13:

Leu His Lys Lys Ala Ala Glu Thr Leu Met Val Leu Asp
1               5                  10

(2) INFORMATION FOR SEQ ID NO:14:

(i) SEQUENCE CHARACTERISTICS:
            (A) LENGTH: 23 amino acids
            (B) TYPE: amino acid
            (C) STRANDEDNESS: single
            (D) TOPOLOGY: linear (xi) SEQUENCE DESCRIPTION: SEQ ID NO:14:

Thr Ala Asp Cys Lys Ile Lys Pro Asn Thr Leu His Lys Lys Ala Ala
1               5                  10                  15

Glu Thr Leu Met Val Leu Asp
            20

(2) INFORMATION FOR SEQ ID NO:15:

(i) SEQUENCE CHARACTERISTICS:
            (A) LENGTH: 30 amino acids
            (B) TYPE: amino acid
            (C) STRANDEDNESS: single
            (D) TOPOLOGY: linear (xi) SEQUENCE DESCRIPTION: SEQ ID NO:15:

Arg Thr Asn Glu His Thr Ala Asp Cys Lys Ile Lys Pro Asn Thr Leu
1               5                  10                  15

His Lys Lys Ala Ala Glu Thr Leu Met Val Leu Asp Gln Asn
            20                  25                  30

(2) INFORMATION FOR SEQ ID NO:16:

(i) SEQUENCE CHARACTERISTICS:
            (A) LENGTH: 11 amino acids
            (B) TYPE: amino acid
            (C) STRANDEDNESS: single
            (D) TOPOLOGY: linear (xi) SEQUENCE DESCRIPTION: SEQ ID NO:16:

Arg Thr Asn Glu His Thr Ala Asp Cys Lys Ile
1               5                   10

(2) INFORMATION FOR SEQ ID NO:17:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (xi) SEQUENCE DESCRIPTION: SEQ ID NO:17:

CGGAA AACGAACAAA TGAACATACG GCAGATTGTA AAATTAAACC GAACACCTTG    60

CATAAAAAAG CTGCAGAGAC TTTAATGGTC                               90

(2) INFORMATION FOR SEQ ID NO:18:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:18:

CGGAA AACGAACAAA TGAACATACG GCAGATTGTA AAATTAAACC GAACACCTTG    60

CATAAAAAAG CTGCA                                               75

(2) INFORMATION FOR SEQ ID NO:19:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:19:

GGGATCGGAA AACGAACAAA TGAACATACG GCAGATTGTA AAATTAAACC GAACACCTTG    60

(2) INFORMATION FOR SEQ ID NO:20:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:20:

GGGATCGGAA AACGAACAAA TGAACATACG GCAGATTGTA AAATT              45

(2) INFORMATION FOR SEQ ID NO:21:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:21:

GGGATCGGAA AACGAACAAA TGAACATACG GCAGATTGTA AA                 42

(2) INFORMATION FOR SEQ ID NO:22:

(i) SEQUENCE CHARACTERISTICS:
        (A) LENGTH: 30 base pairs (B) TYPE: nucleic acid
            (C) STRANDEDNESS: single
            (D) TOPOLOGY: linear (xi) SEQUENCE DESCRIPTION: SEQ ID NO:22:

CGAACAAATG AACATACGGC AGATTGTAAA                                            30

(2) INFORMATION FOR SEQ ID NO:23:

(i) SEQUENCE CHARACTERISTICS:
            (A) LENGTH: 108 base pairs
            (B) TYPE: nucleic acid
            (C) STRANDEDNESS: single
            (D) TOPOLOGY: linear (xi) SEQUENCE DESCRIPTION: SEQ ID NO:23:

GGGATCGGAA AACGAACAAA TGAACATACG GCAGATTGTA AAATTAAACC GAACACCTTG           60

CATAAAAAAG CTGCAGAGAC TTTAATGGTC CTTGACCAAA ATGAACCA                       108

(2) INFORMATION FOR SEQ ID NO:24:

(i) SEQUENCE CHARACTERISTICS:
            (A) LENGTH: 10 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION: /product= "Other"
                /note= "The Xaa at position 1 is N-acetyl arginine."

(ix) FEATURE:
            (A) NAME/KEY: Modified-site
            (B) LOCATION: 10
            (D) OTHER INFORMATION: /product= "Other"
                /note= "The Xaa at position 10 is lysinamide."

(xi) SEQUENCE DESCRIPTION: SEQ ID NO:24:

Xaa Thr Asn Glu His Thr Ala Asp Cys Xaa
1               5                   10

(2) INFORMATION FOR SEQ ID NO:25:

(i) SEQUENCE CHARACTERISTICS:
            (A) LENGTH: 10 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION: /product= "Other"
                /note= "The Xaa at position 1 is N-acetyl arginine."

(ix) FEATURE:
            (A) NAME/KEY: Modified-site
            (B) LOCATION: 10
            (D) OTHER INFORMATION: /product= "Other"
                /note= "The Xaa at position 10 is lysinamide."

(xi) SEQUENCE DESCRIPTION: SEQ ID NO:25:

Xaa Thr Asn Glu His Thr Ala Glu Cys Xaa
1               5                   10

(2) INFORMATION FOR SEQ ID NO:26:

(i) SEQUENCE CHARACTERISTICS:

(A) LENGTH: 10 amino acids
                (B) TYPE: amino acid
                (C) STRANDEDNESS: single
                (D) TOPOLOGY: linear (ix) FEATURE:
                (A) NAME/KEY: Modified-site
                (B) LOCATION: 1
                (D) OTHER INFORMATION: /product= "Other"
                    /note= "The Xaa at position 1 is N-acetyl arginine."

(ix) FEATURE:
                (A) NAME/KEY: Modified-site
                (B) LOCATION: 10
                (D) OTHER INFORMATION: /product= "Other"
                    /note= "The Xaa at position 10 is lysinamide."

(xi) SEQUENCE DESCRIPTION: SEQ ID NO:26:

Xaa Thr Gln Glu His Thr Ala Glu Cys Xaa
1               5                   10

(2) INFORMATION FOR SEQ ID NO:27:

(i) SEQUENCE CHARACTERISTICS:
                (A) LENGTH: 10 amino acids
                (B) TYPE: amino acid
                (C) STRANDEDNESS: single
                (D) TOPOLOGY: linear (ix) FEATURE:
                (A) NAME/KEY: Modified-site
                (B) LOCATION: 1
                (D) OTHER INFORMATION: /product= "Other"
                    /note= "The Xaa at position 1 is N-acetyl arginine."

(ix) FEATURE:
                (A) NAME/KEY: Modified-site
                (B) LOCATION: 10
                (D) OTHER INFORMATION: /product= "Other"
                    /note= "The Xaa at position 10 is lysinamide."

(xi) SEQUENCE DESCRIPTION: SEQ ID NO:27:

Xaa Thr Gln Glu His Thr Ala Asp Cys Xaa
1               5                   10

(2) INFORMATION FOR SEQ ID NO:28:

(i) SEQUENCE CHARACTERISTICS:
                (A) LENGTH: 10 amino acids
                (B) TYPE: amino acid
                (C) STRANDEDNESS: single
                (D) TOPOLOGY: linear (xi) SEQUENCE DESCRIPTION: SEQ ID NO:28:

Arg Thr Asn Glu His Thr Ala Glu Cys Lys
1               5                   10

(2) INFORMATION FOR SEQ ID NO:29:

(i) SEQUENCE CHARACTERISTICS:
                (A) LENGTH: 10 amino acids
                (B) TYPE: amino acid
                (C) STRANDEDNESS: single
                (D) TOPOLOGY: linear (xi) SEQUENCE DESCRIPTION: SEQ ID NO:29:

Arg Thr Gln Glu His Thr Ala Glu Cys Lys
1               5                   10

(2) INFORMATION FOR SEQ ID NO:30:

```
        (i) SEQUENCE CHARACTERISTICS:
            (A) LENGTH: 10 amino acids
            (B) TYPE: amino acid
            (C) STRANDEDNESS: single
            (D) TOPOLOGY: linear (xi) SEQUENCE DESCRIPTION: SEQ ID NO:30:

Arg Thr Gln Glu His Thr Ala Asp Cys Lys
1               5                   10

(2) INFORMATION FOR SEQ ID NO:31:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:31:

AAATG AACATACGGC AGAATGTAAA                                      30

(2) INFORMATION FOR SEQ ID NO:32:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:32:

ACAAG AACATACGGC AGAATGTAAA                                      30

(2) INFORMATION FOR SEQ ID NO:33:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:33:

G AACATACGGC AGATTGTAAA                                          30
```